(12) United States Patent
Sanchez

(10) Patent No.: US 11,534,135 B2
(45) Date of Patent: Dec. 27, 2022

(54) METHODS AND APPARATUSES FOR MONITORING FETAL HEARTBEAT AND UTERINE CONTRACTION SIGNALS

(71) Applicant: BFLY Operations, Inc., Guilford, CT (US)

(72) Inventor: Nevada J. Sanchez, Guilford, CT (US)

(73) Assignee: BFLY OPERATIONS, INC., Burlington, MA (US)

(*) Notice: Subject to any disclaimer, the term of this patent is extended or adjusted under 35 U.S.C. 154(b) by 58 days.

(21) Appl. No.: 17/033,510

(22) Filed: Sep. 25, 2020

(65) Prior Publication Data

US 2021/0093291 A1    Apr. 1, 2021

Related U.S. Application Data

(60) Provisional application No. 62/907,522, filed on Sep. 27, 2019.

(51) Int. Cl.
*A61B 8/08*    (2006.01)
*A61B 8/00*    (2006.01)
(Continued)

(52) U.S. Cl.
CPC ............ *A61B 8/0866* (2013.01); *A61B 8/145* (2013.01); *A61B 8/4236* (2013.01);
(Continued)

(58) Field of Classification Search
CPC ......... A61B 8/145; A61B 5/4356; A61B 8/54; A61B 5/033; A61B 8/0866; A61B 8/4236
See application file for complete search history.

(56) References Cited

U.S. PATENT DOCUMENTS 4,131,021 A * 12/1978 Mezrich ............... A61B 8/00
73/625
8,852,103 B2   10/2014 Rothberg et al.
(Continued)

OTHER PUBLICATIONS

International Search Report and Written Opinion dated Dec. 31, 2020 in connection with International Application No. PCT/US2020/052759.
(Continued)

*Primary Examiner* — Joel Lamprecht
*Assistant Examiner* — Nyrobi Celestine
(74) *Attorney, Agent, or Firm* — Osha Bergman Watanabe & Burton LLP

(57) ABSTRACT

Aspects of the technology described herein related to monitoring fetal heartbeat and uterine contraction signals. An ultrasound system may be configured to sweep a volume to collect ultrasound data, detect a fetal heartbeat and/or uterine contraction signal in the ultrasound data, and automatically steer an ultrasound beam to monitor the fetal heartbeat and/or uterine contraction signal. The ultrasound system may be further configured to determine a location where the fetal heartbeat and/or uterine contraction signal is detectable or detectable at a highest quality. The ultrasound system may include a wearable ultrasound device, such as an ultrasound patch coupled to a subject. The wearable ultrasound device may have a two-dimensional array of ultrasonic transducers capable of steering ultrasound beams in three dimensions.

23 Claims, 15 Drawing Sheets

(51) Int. Cl.
*A61B 8/14* (2006.01)
*A61B 8/02* (2006.01)
*A61B 5/00* (2006.01)

(52) U.S. Cl.
CPC .............. *A61B 8/4494* (2013.01); *A61B 8/52* (2013.01); *A61B 8/56* (2013.01); *A61B 5/4356* (2013.01); *A61B 8/02* (2013.01); *A61B 8/4227* (2013.01); *A61B 8/486* (2013.01)

(56) References Cited

U.S. PATENT DOCUMENTS

| | | |
|---|---|---|
| 9,067,779 B1 | 6/2015 | Rothberg et al. |
| 9,229,097 B2 | 1/2016 | Rothberg et al. |
| 9,232,901 B2* | 1/2016 | Rao ................. A61B 5/725 |
| 9,242,275 B2 | 1/2016 | Rothberg et al. |
| 9,499,392 B2 | 11/2016 | Rothberg et al. |
| 9,505,030 B2 | 11/2016 | Rothberg et al. |
| 9,521,991 B2 | 12/2016 | Rothberg et al. |
| 9,533,873 B2 | 1/2017 | Rothberg et al. |
| 9,592,030 B2 | 3/2017 | Rothberg et al. |
| 9,592,032 B2 | 3/2017 | Rothberg et al. |
| 9,693,690 B2* | 7/2017 | Ater ................. A61B 5/02411 |
| 9,820,718 B2* | 11/2017 | Flomerfelt ............ A61B 8/4236 |
| 10,092,271 B2* | 10/2018 | Lewis, Jr. ............ A61B 8/4494 |
| 10,175,347 B2 | 1/2019 | Chen et al. |
| 10,187,020 B2 | 1/2019 | Chen et al. |
| 10,196,261 B2 | 2/2019 | Rothberg et al. |
| 10,238,362 B2 | 3/2019 | Lahiji et al. |
| 10,695,034 B2 | 6/2020 | Ralston et al. |
| 10,755,692 B2 | 8/2020 | Ralston et al. |
| 2008/0161689 A1* | 7/2008 | Pandit ................. A61B 8/02 600/588 |
| 2008/0208057 A1* | 8/2008 | Hoctor ................. B06B 1/0292 600/453 |
| 2010/0016744 A1* | 1/2010 | Brost ................. A61B 8/4209 600/511 |
| 2011/0055447 A1 | 3/2011 | Costa |
| 2012/0150010 A1 | 6/2012 | Hayes-Gill et al. |
| 2012/0179046 A1 | 7/2012 | Kabakov et al. |
| 2013/0281861 A1* | 10/2013 | Flomerfelt ............ A61B 8/02 600/483 |
| 2014/0243614 A1 | 8/2014 | Rothberg et al. |
| 2016/0213349 A1* | 7/2016 | Groberman ............ A61B 8/02 |
| 2017/0281138 A1 | 10/2017 | Bao et al. |
| 2017/0285152 A1 | 10/2017 | Bao et al. |
| 2017/0307740 A1 | 10/2017 | Ralston et al. |
| 2017/0307741 A1 | 10/2017 | Ralston et al. |
| 2017/0360397 A1 | 12/2017 | Rothberg et al. |
| 2017/0360399 A1 | 12/2017 | Rothberg et al. |
| 2018/0070917 A1 | 3/2018 | Rothberg et al. |
| 2018/0271476 A1 | 9/2018 | Strassner et al. |
| 2018/0376253 A1 | 12/2018 | Lutsky et al. |
| 2019/0001159 A1 | 1/2019 | Chen et al. |
| 2019/0069842 A1 | 3/2019 | Rothberg et al. |
| 2019/0133549 A1* | 5/2019 | Hamelmann ........ A61B 8/0883 |
| 2019/0142387 A1 | 5/2019 | Chen et al. |
| 2019/0282207 A1 | 9/2019 | Chen et al. |
| 2019/0343484 A1 | 11/2019 | Rothberg et al. |

OTHER PUBLICATIONS

Peters et al., Monitoring the fetal heart noninvasively: A review of methods. Journal of Perinatal Medicine. Feb. 2001; 29(5):408-16.
International Preliminary Report on Patentability dated Apr. 7, 2022 in connection with International Application No. PCT/US2020/052759.

* cited by examiner

METHODS AND APPARATUSES FOR MONITORING FETAL HEARTBEAT AND UTERINE CONTRACTION SIGNALS

CROSS-REFERENCE TO RELATED APPLICATIONS

The present application claims the benefit under 35 U.S.C. § 119(e) of U.S. Patent Application Ser. No. 62/907,522, filed Sep. 27, 2019 and entitled "METHODS AND APPARATUSES FOR MONITORING FETAL HEARTBEAT AND UTERINE CONTRACTION SIGNALS," which is hereby incorporated by reference herein in its entirety.

FIELD

Generally, the aspects of the technology described herein relate to ultrasound systems and devices. Certain aspects relate to ultrasound systems and devices for monitoring fetal heartbeat and/or uterine contraction signals.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the application, an apparatus includes an ultrasound system configured to sweep a volume to collect ultrasound data, detect a fetal heartbeat and/or uterine contraction signal in the ultrasound data; and automatically steer an ultrasound beam to monitor the fetal heartbeat and/or uterine contraction signal.

In some embodiments, the ultrasound data includes multiple sets of ultrasound data collected at different locations within the volume. In some embodiments, the ultrasound system is further configured to determine a location where the fetal heartbeat and/or uterine contraction signal is detectable or detectable at a highest quality. In some embodiments, the ultrasound system is further configured to sweep a modified volume to collect ultrasound data. In some embodiments, the ultrasound system is further configured to determine a location where the fetal heartbeat and/or uterine contraction signal is detectable or detectable at the highest quality; and the ultrasound system is configured, when sweeping the modified volume to collect ultrasound data, to sweep a volume modified based on the location where the fetal heartbeat and/or uterine contraction signal was previously monitored. In some embodiments, the modified volume is collected with a sweep that is centered around the location where the fetal heartbeat and/or uterine contraction signal was previously monitored.

In some embodiments, the ultrasound system includes a wearable ultrasound device. In some embodiments, the wearable ultrasound device includes an ultrasound patch coupled to a subject. In some embodiments, the wearable ultrasound device has a two-dimensional array of ultrasonic transducers. In some embodiments, the ultrasound system includes a processing device in communication with an ultrasound device. In some embodiments, the processing device includes a mobile phone, tablet, laptop, or a processing device of a standard cardiotocography (CTG) system. In some embodiments, the processing device includes the processing device of the standard cardiotocography system, the ultrasound device includes an output port configured to couple to one end of a cable, and another end of the cable is configured to be coupled to the processing device of the standard CTG system.

According to another aspect of the application, an apparatus includes an ultrasound system configured to configure an ultrasound device to collect multiple sets of ultrasound data from multiple regions within a subject, detect fetal heartbeat and/or uterine contraction signals from the collected sets of ultrasound data, and monitor the fetal heartbeat and/or uterine contraction signals by automatically configuring the ultrasound device to collect further ultrasound data from a region within the subject corresponding to one of the multiple sets of ultrasound data based on a quality of its fetal heartbeat and/or uterine contraction signal.

In some embodiments, the ultrasound system is configured, when configuring the ultrasound device to collect the multiple sets of ultrasound data from the multiple regions within the subject, to collect each of the multiple sets of ultrasound data from a particular region within the subject. In some embodiments, each of the multiple sets of ultrasound data includes a time series of an A-line. In some embodiments, the time series is over a sufficiently long period to capture heartbeat motion. In some embodiments, each of the multiple sets of data includes a time series of ultrasound images collected from a two-dimensional slice within the subject.

In some embodiments, the ultrasound system is configured, when detecting the fetal heartbeat signals from the collected sets of ultrasound data, to use an M-mode ultrasound technique. In some embodiments, the ultrasound system is configured, when detecting the fetal heartbeat signals from the collected sets of ultrasound data, to use a statistical model that is trained to detect fetal heartbeat signals in ultrasound data. In some embodiments, the ultrasound system is configured, when detecting the uterine contraction signals from the collected sets of ultrasound data, to use a speckle tracking technique to analyze the ultrasound data for tissue contraction. In some embodiments, the ultrasound system is configured, when detecting the uterine contraction signals from the collected sets of ultrasound data, to use a statistical model that is trained to measure a thickness of muscle around a uterus in ultrasound images.

In some embodiments, the ultrasound system is configured, when automatically configuring the ultrasound device to collect the further ultrasound data from the region within the subject corresponding to one of the multiple sets of ultrasound data based on the quality of its fetal heartbeat and/or uterine contraction signal, to configure the ultrasound device to use a two-dimensional array of ultrasonic transducers to steer an ultrasound beam in three dimensions to the region in order to collect the further ultrasound data. In some embodiments, the ultrasound system is configured, when automatically configuring the ultrasound device to collect the further ultrasound data from the region within the subject corresponding to one of the multiple sets of ultrasound data based on the quality of its fetal heartbeat and/or uterine contraction signal, to configure the ultrasound device to collect the further ultrasound data without collecting ultrasound data from other of the multiple regions within the subject. In some embodiments, the ultrasound system is configured to monitor the fetal heartbeat and/or uterine contraction signals for a period of time. In some embodiments, the ultrasound system is configured, when automatically configuring the ultrasound device to collect the further ultrasound data from the region within the subject corresponding to one of the multiple sets of ultrasound data based on the quality of its fetal heartbeat and/or uterine contraction signal, to configure the ultrasound device to collect the further ultrasound data from a region within the subject corresponding to a set of ultrasound data that has a highest quality fetal heartbeat signal. In some embodiments, the ultrasound system is configured, when automatically configuring the ultrasound device to collect the further ultrasound data from the region within the subject corresponding to one of the multiple sets of ultrasound data based on the quality of its fetal heartbeat and/or uterine contraction signal, to configure the ultrasound device to collect the further ultrasound data from a region within the subject corresponding to a set of ultrasound data that has a highest quality uterine contraction signal. In some embodiments, the ultrasound system is configured, when automatically configuring the ultrasound device to collect the further ultrasound data from the region within the subject corresponding to one of the multiple sets of ultrasound data based on the quality of its fetal heartbeat and/or uterine contraction signal, to configure the ultrasound device to collect the further ultrasound data from a region within the subject corresponding to a set of ultrasound data that has a highest combined quality of fetal heartbeat and uterine contraction signals. In some embodiments, the combined quality of the fetal heartbeat and uterine contraction signals is a mean of a quality of the fetal heartbeat signal and a quality of the uterine contraction signal. In some embodiments, the quality of the fetal heartbeat signal is based on a signal-to-noise ratio (SNR) of the fetal heartbeat signal. In some embodiments, the quality of the fetal heartbeat signal is based on a level of confidence of a statistical model that the statistical model has accurately determined the fetal heartbeat signal from the further ultrasound data. In some embodiments, the quality of the uterine contraction signal is based on a signal-to-noise ratio (SNR) of the uterine contraction signal. In some embodiments, the quality of the uterine contraction signal is based on a level of confidence of a statistical model that the statistical model has accurately measured a thickness of a muscle around a uterus.

In some embodiments, the ultrasound system is further configured to continuously or periodically monitor a quality of the fetal heartbeat and/or uterine contraction signals, and to configure the ultrasound device to collect multiple sets of ultrasound data from a subset of the multiple regions within the subject based on the quality of the fetal heartbeat and/or uterine contraction signals not exceeding a threshold quality. In some embodiments, the ultrasound system is further configured to configure the ultrasound device to collect multiple sets of ultrasound data from a subset of the multiple regions within the subject. In some embodiments, the ultrasound system is configured to select the subset of the regions based on the region from which the further ultrasound data was collected. In some embodiments, the subset of the regions is a first particular percentage of regions approximately centered around the region within the subject from which the further ultrasound data was collected. In some embodiments, the subset of the regions is along a spiral curve around the region within the subject from which the further ultrasound data was collected.

In some embodiments, the ultrasound system is configured to monitor the fetal heartbeat and uterine contraction signals from different regions within the subject. In some embodiments, the ultrasound system is configured to steer an ultrasound beam to one region to monitor the fetal heartbeat signal and to steer the ultrasound beam to another region to monitor the uterine contraction signal. In some embodiments, the ultrasound system is configured to monitor the fetal heartbeat signal at a higher sampling rate than a sampling rate at which the uterine contraction signal is monitored.

In some embodiments, the ultrasound system is further configured to output the fetal heartbeat and/or uterine contraction signals for display. In some embodiments, the ultrasound system is configured to transmit the fetal heartbeat and/or uterine contractions over a communication link to a processing device configured to display the fetal heartbeat signal and/or uterine contraction signals as one or more graphs on its display screen. In some embodiments, the processing device includes a mobile phone, tablet, laptop, or a processing device of a standard cardiotocography system. In some embodiments, the processing device includes the processing device of the standard cardiotocography system, the ultrasound device includes an output port configured to couple to one end of a cable, and another end of the cable is configured to be coupled to the processing device of the standard CTG system.

In some embodiments, the ultrasound system includes a wearable ultrasound device. In some embodiments, the wearable ultrasound device includes an ultrasound patch coupled to a subject. In some embodiments, the wearable ultrasound device has a two-dimensional array of ultrasonic transducers. In some embodiments, the ultrasound system includes a processing device in communication with an ultrasound device. In some embodiments, the processing device includes a mobile phone, tablet, laptop, or a processing device of a standard cardiotocography system. In some embodiments, the processing device includes the processing device of the standard cardiotocography system, the ultrasound device includes an output port configured to couple to one end of a cable, and another end of the cable is configured to be coupled to the processing device of the standard CTG system.

Some aspects include a method to perform the actions that the ultrasound system is configured to perform.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
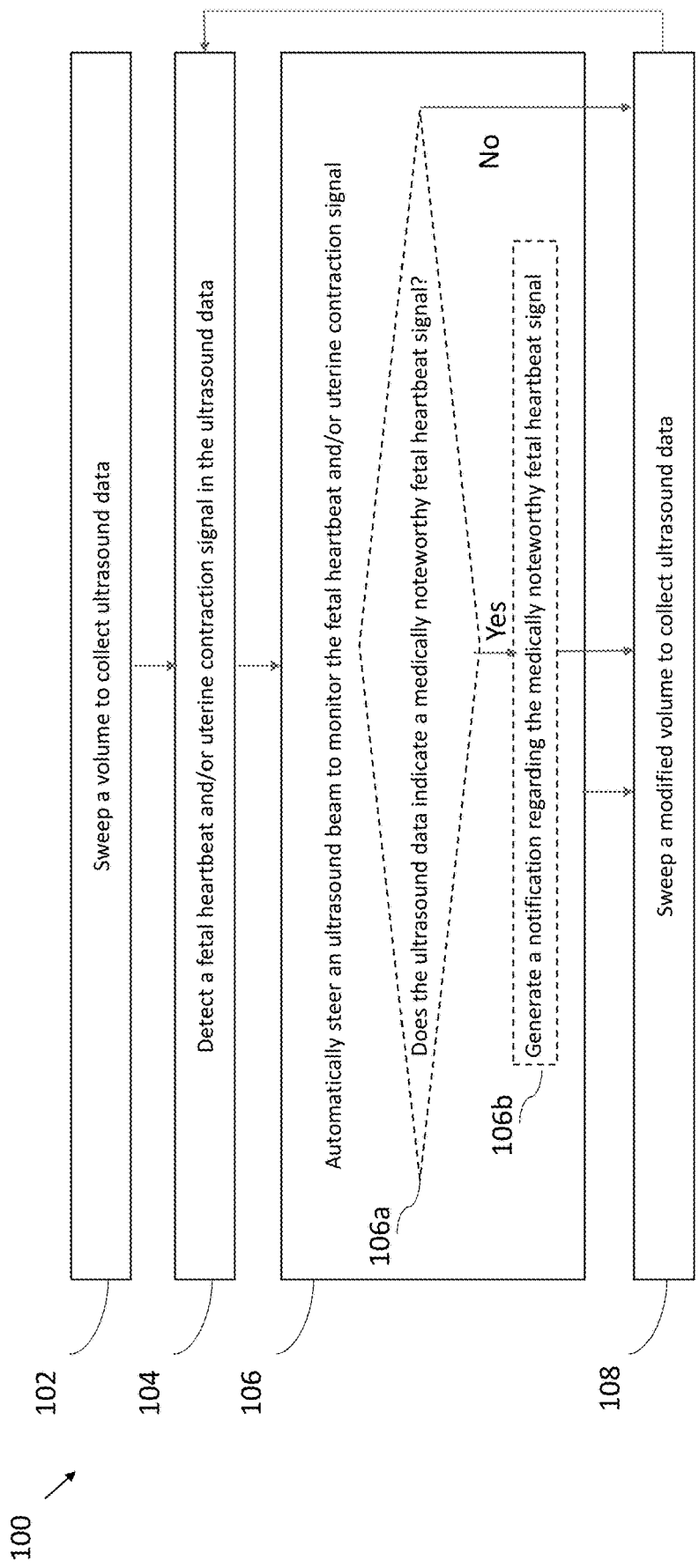
FIG. 1 is a flow diagram illustrating an example process for monitoring a fetal heartbeat or uterine contraction signal, in accordance with certain embodiments described herein.

During labor, it may be desirable to monitor fetal heartbeat and/or uterine contraction signals. While transducers in a cardiotocography system can be coupled adjacent to a subject's uterus for monitoring such signals, due to movement of the subject and/or the fetus, a transducer may be able to detect the fetal heartbeat and/or uterine contraction signals at one location on the subject but not be able to detect the signals a period of time later. Thus, frequent manual readjustment of the positions of the transducers may be needed. The same need to readjust the positions of transducers may also occur during extended at home monitoring (e.g., in the case of a high-risk pregnancy) of fetal heartbeat and/or uterine contraction signals before labor.

Recently, ultrasound-on-chips incorporating ultrasound circuitry and a two-dimensional array of a large number of ultrasonic transducers on an integrated circuit have been developed. The large ultrasound transducer array may allow such an ultrasound-on-chip to have advanced imaging functionality. For example, the two-dimensional ultrasound transducer array may enable an ultrasound beam to be steered in three dimensions and collect three-dimensional ultrasound data from a volume within the subject. The ultrasound-on-chip may be sufficiently small in size to form the core of a wearable ultrasound device. The wearable ultrasound device may be in the form-factor of an ultrasound patch or some other form-factor that can couple to a subject. In some embodiments, the wearable ultrasound device may be self-contained in that it may include ultrasound transducers, transmit circuitry, and receive circuitry, a portion or all of which may be included in an ultrasound-on-chip. The transmit circuitry may include, for example, high-voltage pulsers configured to drive the ultrasonic transducers to emit ultrasound. The receive circuitry may include, for example, analog and digital circuitry configured to (in no particular order) receive analog ultrasound signals; digitize the analog ultrasound signals; filter compress, beamform, and/or form ultrasound images from ultrasound signals; and control and coordinate different parts of the circuitry to work in synchronization with one another. In some embodiments, the wearable ultrasound device may be capable of generating ultrasound images from ultrasound signals it itself collects with ultrasound transducers located on the wearable ultrasound device. In some embodiments, the wearable ultrasound device may not be coupled to another processing device.

In some embodiments, such a wearable ultrasound device may be less than 1 kg in weight. In some embodiments, such a wearable ultrasound device may be less than 0.5 kg in weight. In some embodiments, such a wearable ultrasound device may be less than 0.25 kg in weight. In some embodiments, such a wearable ultrasound device may be less than 5 cm in thickness. In some embodiments, such a wearable ultrasound device may be less than 2.5 cm in thickness. In some embodiments, such a wearable ultrasound device may be less than 1.25 cm in thickness. In some embodiments, such a wearable ultrasound device may be less than 1 cm in thickness. In some embodiments, such a wearable ultrasound device may be less than 180 $cm^3$ in volume. In some embodiments, such a wearable ultrasound device may be less than 90 $cm^3$ in volume. In some embodiments, such a wearable ultrasound device may be less than 45 $cm^3$ in volume. In some embodiments, such a wearable ultrasound device may be less than 25 $cm^3$ in volume. In some embodiments, such a wearable ultrasound device may be less than 15 $cm^3$ in volume. In some embodiments, such a wearable ultrasound device may be less than 6 $cm^3$ in volume.

For further description of ultrasound-on-chips, see U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 (and assigned to the assignee of the instant application) and/or U.S. patent application Ser. No. 16/192,603 titled "ULTRASOUND APPARATUSES AND METHODS FOR FABRICATING ULTRASOUND DEVICES," filed on Nov. 15, 2018 and published as U.S. Pat. App. Publication No. 2019-0142387 A1, both of which are incorporated by reference herein in their entireties.

The inventors have recognized that such a wearable ultrasound device (e.g., a patch) including an ultrasound-on-chip may be configured as a fetal heart and/or uterine contraction monitor. In particular, the inventors have recognized that the capability of the wearable ultrasound device, with the two-dimensional ultrasound transducer array of its ultrasound-on-chip, to steer ultrasound beams in three dimensions may enable the wearable ultrasound device to automatically track fetal heartbeat and/or uterine contraction signals as the subject and/or fetus move. In some embodiments, the wearable ultrasound device may be configured to implement searching algorithms that may scan the image space to find the fetal heartbeat and/or uterine contraction signal, and then implement tracking algorithms to keep the signal in focus while the signal is monitored. Scanning the image space may include collecting ultrasound data from a volume within the subject to find a location where the strongest fetal heartbeat and/or uterine contraction signal may be detected. The wearable ultrasound device may then automatically steer an ultrasound beam to that location. Keeping the signal in focus while the signal is monitored may include periodically collecting ultrasound data from a smaller volume near the previously monitored location to determine if, due to movement of the subject and/or fetus, the ultrasound beam should be re-steered to a new location where the strongest fetal heartbeat and/or uterine contraction signal may be detected.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIGS. 1-7 are flow diagrams illustrating example processes 100-700 for monitoring a fetal heartbeat or uterine contraction signal, in accordance with certain embodiments described herein. The process 100 is a general process and further detail of the process 100 may be found with reference to the processes 200-700. The processes 100-700 are performed by an ultrasound system. The ultrasound system includes an ultrasound device configured to collect ultrasound data from a subject. In some embodiments, the ultrasound device may be a wearable ultrasound device such as an ultrasound patch coupled to a subject, and in particular, to a region adjacent to the subject's uterus. In some embodiments, the ultrasound device may include an ultrasound-on-chip. In some embodiments, the ultrasound system may also include a processing device in communication with the ultrasound device. The processing device may be, for example, a mobile phone, tablet, laptop, the processing device of a standard cardiotocography (CTG) system (e.g., the portions of a CTG system excluding the transducers), or another type of electronic device in communication with the ultrasound device. In embodiments that include an ultrasound device and a processing device, the ultrasound device and the processing device may communicate over a wired communication link (e.g., over Ethernet, a Universal Serial Bus (USB) cable or a Lightning cable) or over a wireless communication link (e.g., over a BLUETOOTH, WiFi, ZIGBEE, or cellular (e.g., 3G, LTE, or CAT-M1) wireless communication link). In embodiments in which the processing device is a processing device of a standard CTG system, the ultrasound device may include an output port configured to couple to one end of a cable, the other end of which is configured to be coupled to the processing device of the CTG system. For example, in the case of USB communication, the ultrasound device may include a USB port and circuitry capable of communication according to the USB protocol. In some embodiments, the ultrasound system may not include a processing device. In some embodiments, the processing device may perform all of the processes 100-700. In some embodiments, the ultrasound device (e.g., an ultrasound patch) may perform the processes 100-700. In some embodiments, the ultrasound device may perform portions of the processes 100-700 and the processing device may perform other portions of the processes 100-700. Any of the processes 100-700 may be used, for example, for monitoring fetal heartbeat and/or uterine contraction signals during labor or for extended at home monitoring (e.g., in the case of a high-risk pregnancy).

In act 102 of the process 100, the ultrasound system sweeps a volume to collect ultrasound data. The ultrasound data may include multiple sets of ultrasound data collected at different locations within the volume. In some embodiments, the processing device may configure the ultrasound device to sweep the volume to collect the ultrasound data. In some embodiments, the ultrasound device may configure itself to sweep the volume to collect the ultrasound data. The process 100 proceeds from act 102 to act 104.

In act 104, the ultrasound system detects a fetal heartbeat and/or uterine contraction signal in the ultrasound data collected in act 102. The ultrasound system may determine the location where the fetal heartbeat and/or uterine contraction signal is detectable and/or detectable at the highest quality. In some embodiments, the processing device may detect the fetal heartbeat and/or uterine contraction signal in the ultrasound data. In some embodiments, the ultrasound device may detect the fetal heartbeat and/or uterine contraction signal in the ultrasound data. The process 100 proceeds from act 104 to act 106.

In act 106, the ultrasound system automatically steers an ultrasound beam to monitor the fetal heartbeat and/or uterine contraction signal that was detected in act 104. In particular, the ultrasound system may steer the ultrasound beam to the location that was determined in act 104. In some embodiments, the processing device may configure the ultrasound device to steer the ultrasound beam to monitor the fetal heartbeat and/or uterine contraction signal. In some embodiments, the ultrasound device may configure itself to steer the ultrasound beam to monitor the fetal heartbeat and/or uterine contraction signal.

As illustrated in FIG. 1, the ultrasound system at act 106 may, optionally, also perform acts 106a and 106b. In act 106a, the ultrasound system determines whether the monitored fetal heartbeat signal indicates a medically noteworthy fetal heartbeat signal. In some embodiments, to make this determination, the ultrasound device may determine the fetal heart rate from the fetal heartbeat signal, and then determine whether the fetal heart rate is medically noteworthy. For example, a medically noteworthy fetal heart rate may be a heart rate that exceeds a certain threshold heart rate or is below a certain threshold heart rate. If the ultrasound system determines that the monitored fetal heartbeat signal indicates a medically noteworthy fetal heartbeat signal, then process 100 proceeds to act 108. If the ultrasound system determines that the monitored fetal heartbeat signal indicates a medically noteworthy fetal heartbeat signal, then process 100 proceeds to act 106b, in which the ultrasound system generates a notification regarding the medically noteworthy fetal heartbeat signal. In some embodiments, the ultrasound device may perform the determination in act 106a and generate the notification in act 106b and, as part of act 106b, transmit the notification to the processing device over a wired communication link (e.g., over Ethernet, a Universal Serial Bus (USB) cable or a Lightning cable) or over a wireless communication link (e.g., over a BLUETOOTH, WiFi, ZIGBEE, or cellular (e.g., 3G, LTE, or CAT-M1) wireless communication link. In some embodiments, the processing device may perform the determination in act 106a and generate the notification in act 106b. The notification may include, for example, a display on the processing device of the fetal heart rate, a display as to whether the heart rate is too high or too low, and/or an auditory alarm generated by the processing device. However, other forms of notifications may be used as well. The process proceeds from act 106b to act 108. If the ultrasound system does not perform acts 106a and 106b, then the process 100 proceeds from act 106 to 108. While acts 106a and 106b are described and illustrated with regards to medically noteworthy fetal heartbeat signals, in other embodiments acts 106a and 106b may determine medically noteworthy uterine contraction signals and generate notifications regarding the same.

The ultrasound system may monitor the fetal heartbeat and/or uterine contraction signal in act 106 for a period of time. However, after the period of time, due to movement of the fetus and/or the subject, the fetal heartbeat and/or uterine contraction may no longer be detectable, or detectable at a sufficient level of quality, or detectable at the highest available level of quality, at the location to which the ultrasound system steered the ultrasound beam in act 106. Accordingly, in act 108, the ultrasound system sweeps a modified volume to collect ultrasound data. The sweep may be modified from the sweep in act 102 based on the location the fetal heartbeat and/or uterine contraction signal was previously monitored in act 106. For example, the modified volume may be a smaller volume that is centered around the previous monitoring location. Thus, the sweep in act 108 may be considered a narrow sweep, while the sweep in act 102 may be considered a wide sweep. The process proceeds from act 108 back to act 104. Thus, after performing the modified sweep in act 108, in act 104, the ultrasound system detects the fetal heartbeat and/or uterine contraction signal from the sweep again, and in act 106, the ultrasound system steers the ultrasound beam (potentially to a different location than the previous location) for further monitoring.

Figure 2:
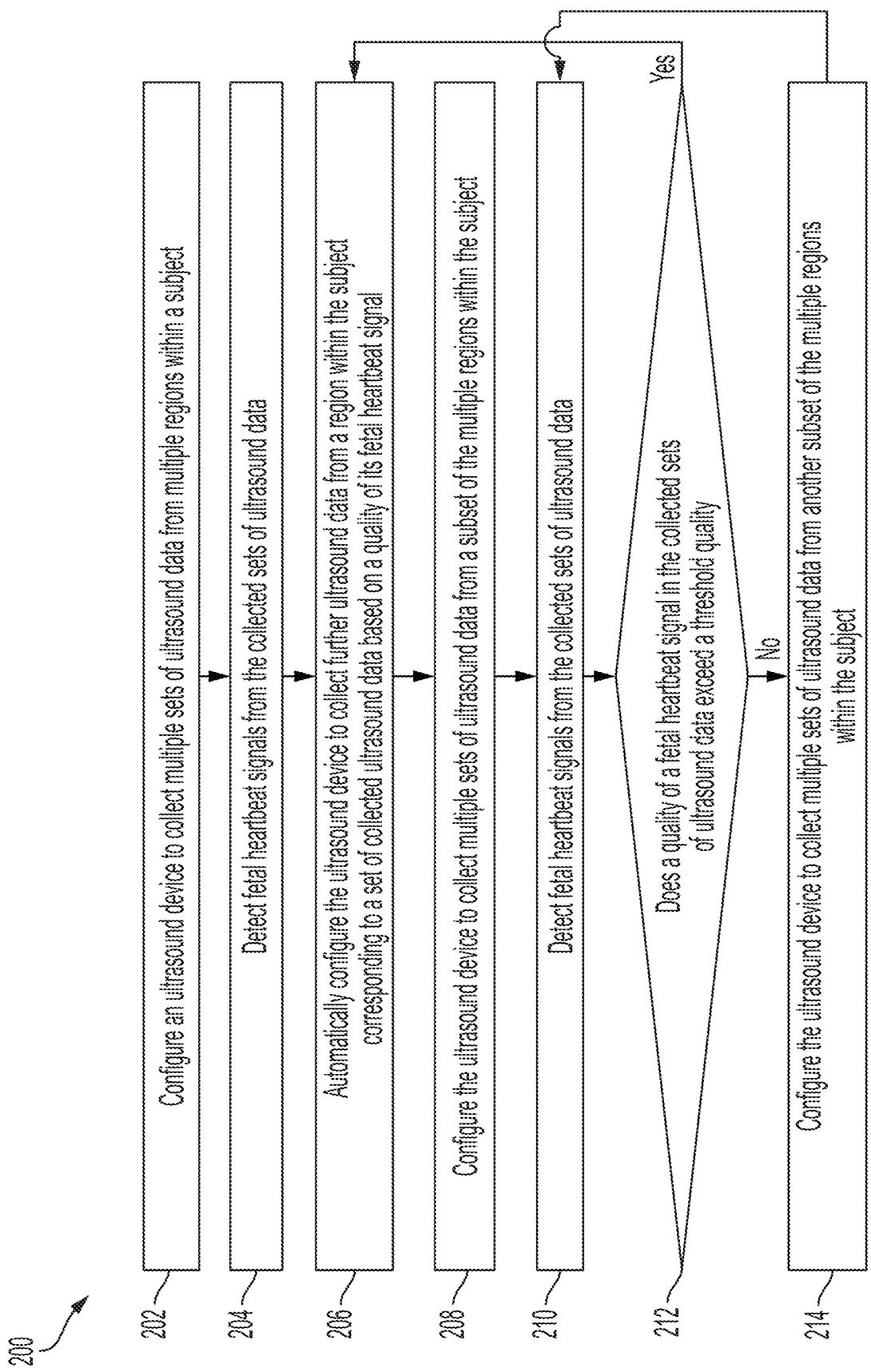
FIG. 2 is another flow diagram illustrating an example process for monitoring a fetal heartbeat or uterine contraction signal, in accordance with certain embodiments described herein.

Referring now to FIG. 2, in the process 200, act 202 may correspond to act 102, act 204 may correspond to act 104, act 206 may correspond to act 106, and acts 208-214 and 216 may correspond to act 108.

In act 202 of the process 200, the ultrasound system configures the ultrasound device to collect multiple sets of ultrasound data from multiple regions within a subject. As referred to herein, a region may be any set of locations. Each set of ultrasound data may be collected from a particular region within the subject. The ultrasound system may be considered to perform an ultrasound sweep in act 202. In some embodiments, the ultrasound device may configure itself to collect the multiple sets of ultrasound data. In some embodiments, a processing device in communication with the ultrasound device may configure the ultrasound device (e.g., by transmitting commands over a communication link) to collect the multiple sets of ultrasound data. In some embodiments, each of the multiple sets of data may be a time series of an A-line. The ultrasound system may configure the ultrasound device to collect the multiple A-lines through rastering along a single dimension, multiple dimensions, or through scanning along a curve (e.g., a spiral) in space. The time series may be over a sufficiently long period to capture heartbeat motion. In some embodiments, each of the multiple sets of data may be a time series of ultrasound images collected from a two-dimensional slice within the subject. Ultrasound images from each of the two-dimensional slices may be collected at a different elevational angle or azimuthal angle with respect to a transducer array of the ultrasound device. In some embodiments, collecting ultrasound images from a two-dimensional slice may include raster collection of A-lines along a single dimension. In some embodiments, collecting ultrasound images from a two-dimensional slice include multiple raster collections of A-lines at multiple different angles with respect to a transducer array of the ultrasound device, using techniques such as spatial compounding. In some embodiments, collecting ultrasound images from a two-dimensional slice may include raster collection of ultrasound data using illumination techniques such as plane waves or diverging beams which may not necessarily be focused A-lines. In some embodiments, collecting ultrasound images from a two-dimensional slice may include using techniques such as synthetic aperture techniques, where reconstruction along a particular direction may not be complete until several directions have been combined with it. In some embodiments, multiple sets of ultrasound images from multiple two-dimensional slices may together constitute a three-dimensional volume. The process 200 proceeds from act 202 to act 204.

In act 204, the ultrasound system detects fetal heartbeat signals from the sets of ultrasound data collected in act 202. In some embodiments, detecting fetal heartbeat signals may include using an M-mode ultrasound technique. In embodiments in which the ultrasound data includes A-lines, the M-mode ultrasound technique may be applied directly to the A-lines. In embodiments in which the ultrasound data includes ultrasound images from two-dimensional slices, the M-mode technique may be applied to particular A-lines within the two-dimensional ultrasound images. In some embodiments, detecting fetal heartbeat signals may include using a statistical model that is trained to detect fetal heartbeat signals in ultrasound data. For example, the statistical model may be trained to classify ultrasound images as belonging to a particular phase of the heartbeat cycle (e.g., systole or diastole), and the heartbeat signal (e.g., the heartrate) may be detected by determining the time between successive beginnings of the phase of the heartbeat cycle. Any of the statistical models discussed herein may be, for example, a convolutional neural network, a fully connected neural network, a recurrent neural network (e.g., a long short-term memory (LSTM) recurrent neural network), a random forest, a support vector machine, a linear classifier, and/or any other statistical model. Any of the statistical models described in this application may be stored and run on the ultrasound device. For example, the ultrasound device may include one or more chips designed for operating statistical models. The chips may be artificial intelligence (AI) accelerator chips, such as tensor processing units (TPUs)). Alternatively, any of the statistical models described in this application may be stored and run on a processing device in communication with the ultrasound device or on an electronic device accessed by the ultrasound device or the processing device. Further description of detecting fetal heartbeat signals may be found in Peters et. al., Monitoring the fetal heart non-invasively: A review of methods, Journal of perinatal medicine, 2001, the content of which is incorporated by reference herein in its entirety. In some embodiments, the ultrasound device may perform the detection in act 204. In some embodiments, a processing device in communication with the ultrasound device may perform the detection in act 204. The process 200 proceeds from act 204 to act 206.

In act 206, the ultrasound system automatically configures the ultrasound device to collect further ultrasound data from a region within the subject. The region corresponds to a set of ultrasound data based on a quality of its fetal heartbeat signal. The region may be the region from which the set of ultrasound data was collected in act 202. The ultrasound system may configure the ultrasound device to use its two-dimensional array of ultrasonic transducers to steer an ultrasound beam in three dimensions to the region in order to collect the further ultrasound data. The ultrasound system may configure the ultrasound device to collect this ultrasound data without collecting ultrasound data from the other regions from which ultrasound data was collected in act 202. Based on the ultrasound data collected in act 206, the ultrasound system may detect a fetal heartbeat signal (e.g., using the techniques described with reference to act 204). Thus, act 206 may constitute monitoring of the fetal heartbeat signal, and may be performed for a period of time. In some embodiments, the quality of a fetal heartbeat signal may be based on the signal-to-noise ratio (SNR) of the fetal heartbeat signal (e.g., the SNR of the M-mode data from which the fetal heartbeat signal is determined). In some embodiments, the quality of a fetal heartbeat signal may be based on the level of confidence of a statistical model that the statistical model has accurately determined the fetal heartbeat signal from ultrasound data. For example, the level of confidence may be related to a level of confidence the statistical model has that it has accurately classified ultrasound images as belonging to a particular phase of the heartbeat cycle (e.g., systole or diastole). In some embodiments, the ultrasound system may configure the ultrasound device to collect further ultrasound data from a region within the subject corresponding to a set of ultrasound data that has the highest quality. In some embodiments, the ultrasound device may determine the quality in act 206. In some embodiments, a processing device in communication with the ultrasound device may determine the quality in act 206. In some embodiments, the ultrasound device may configure itself to collect the further ultrasound data. In some embodiments, a processing device in communication with the ultrasound device may configure the ultrasound device to collect the further ultrasound data (e.g., by transmitting commands over a communication link). The process 200 proceeds from act 206 to act 208.

The ultrasound system may collect further ultrasound data, and thereby monitor the fetal heartbeat signal, in act 206 for a period of time. However, due to movement of the fetus and/or the subject, the fetal heartbeat may no longer be detectable, or no longer be detectable at a sufficient level of quality, or no longer be detectable at the highest available level of quality, at the region from which the ultrasound system is collecting data in act 206. Accordingly, the ultrasound system performs another ultrasound sweep in act 208. Act 208 may occur a set period of time after act 206 (i.e., after a set period of monitoring). Based on the assumption that the fetus and/or subject has not moved an extreme amount during the monitoring period, the ultrasound system may not perform a sweep over all the regions from act 202. Instead, the ultrasound system performs a modified sweep over a subset of these locations, in which the ultrasound system may search around the previously monitored region. Thus, the sweep of act 202 may be considered a wide sweep while the sweep of act 208 may be considered a narrow sweep.

In some embodiments, the narrow sweep may be any sweep that is smaller than the wide sweep. For example, consider that the wide sweep and narrow sweep are sweeps of A-lines. In some embodiments, the wide sweep may be over a span in the azimuthal direction, elevational direction, or both azimuthal and elevation directions (i.e., defining a solid angle) of 40 degrees, 50 degrees, 60 degrees, 70 degrees, 80 degrees, 90 degrees, 100 degrees, 110 degrees, 120 degrees, or any other span of degrees in between these values. In some embodiments, the narrow sweep may be over a span in the azimuthal direction, elevational direction, or both azimuthal and elevation directions (i.e., defining a solid angle) of 5 degrees, 10 degrees, 15 degrees, or any other span of degrees in between these values. (It should be appreciated that a sweep that spans X degrees may mean that the sweep proceeds from –X/2 to X/2 degrees.) As another example, consider that the wide sweep and narrow sweep are sweeps of ultrasound images. In some embodiments, the wide sweep may be over a span in the elevational direction of 40 degrees, 50 degrees, 60 degrees, 70 degrees, 80 degrees, 90 degrees, 100 degrees, 110 degrees, 120 degrees, or any other span of degrees in between these values. In some embodiments, the narrow sweep may be over a span in the elevational direction of 5 degrees, 10 degrees, 15 degrees, or any other span of degrees in between these values.

In act 208, the ultrasound system configures the ultrasound device to collect multiple sets of ultrasound data from a subset of the multiple regions within the subject (from which ultrasound data was collected in act 202). In some embodiments, the ultrasound system may select the subset of the regions based on the region from which further ultrasound data was collected in act 206 (which may be referred to hereinafter as "the monitored region"). In some embodiments, the ultrasound system may configure the ultrasound device to collect ultrasound data from X % (where X is a number between 0 and 100) of the regions from which ultrasound data was collected in act 202. In some embodiments, the subset of the regions may be the first X % of the regions that are approximately centered around the monitored region. For example, the ultrasound system may configure the ultrasound device to collect ultrasound data with raster scanning, and the approximate center of the raster scan may be the monitored region. As another example, the ultrasound system may configure the ultrasound device to collect ultrasound data along a spiral curve around the monitored region. In some embodiments, the ultrasound device may configure itself to collect the multiple sets of ultrasound data. In some embodiments, a processing device in communication with the ultrasound device may configure the ultrasound device (e.g., by transmitting commands over a communication link) to collect the multiple sets of ultrasound data. The process 200 proceeds from act 208 to act 210.

In act 210, the ultrasound system detects fetal heartbeat signals from the sets of ultrasound data collected in act 208. Further description of detecting fetal heartbeat signals may be found with reference to act 204. The process 200 proceeds from act 210 to act 212.

In act 212, the ultrasound system determines whether a quality of a fetal heartbeat signal in the collected sets of ultrasound data (from act 208) exceeds a threshold quality. Regarding the quality of a fetal heartbeat signal, in some embodiments, the ultrasound system may determine whether a signal-to-noise ratio (SNR) of a fetal heartbeat signal (e.g., the SNR of the M-mode data from which the fetal heartbeat signal is determined) in any of the collected ultrasound data exceeds a threshold SNR. In some embodiments, the ultrasound system may determine whether a statistical model has accurately determined the fetal heartbeat signal from any of the collected ultrasound data with a level of confidence exceeding a threshold level of confidence. In some embodiments, the ultrasound device may perform the determination in act 212. In some embodiments, a processing device in communication with the ultrasound device may perform the determination in act 212. If the ultrasound system determines that a quality of fetal heartbeat signal in the collected ultrasound data exceeds a threshold quality, the process 200 proceeds from act 212 to act 206. In act 206, the ultrasound system again performs monitoring of the fetal heartbeat, but may collect ultrasound data for this monitoring from a different region than in the previous iteration through act 206. In some embodiments, the ultrasound system may configure the ultrasound device to collect further ultrasound data from a region within the subject corresponding to a set of ultrasound data collected in act 208 that has the highest quality. If the ultrasound system determines that a quality of a fetal heartbeat signal in the collected ultrasound data does not exceed a threshold quality, the process 200 proceeds from act 212 to act 214.

In act 214, the ultrasound system configures the ultrasound device to collect multiple sets of ultrasound data from another subset of the multiple regions within the subject (i.e., different from the subset of act 208). In some embodiments, the ultrasound system may configure the ultrasound device to collect ultrasound data from the next Y % regions (i.e., the next Y % after the first X %, where Y is a number between 0 and 100−X) from which ultrasound data was collected in act 202. In some embodiments, the subset of the regions may be the next Y % of the regions that are centered around the monitored region. In other words, the ultrasound system may search further (compared with the search from act 208) around the monitored region. In some embodiments, the ultrasound device may configure itself to collect the multiple sets of ultrasound data. In some embodiments, a processing device in communication with the ultrasound device may configure the ultrasound device (e.g., by transmitting commands over a communication link) to collect the multiple sets of ultrasound data. The process proceeds from act 214 to act 210, in which the ultrasound system detects fetal heartbeat signals from the sets of ultrasound data collected in act 214.

In some embodiments, acts 208-214 may be absent. For example, the ultrasound system may configure the ultrasound device to collect ultrasound data from a particular region in act 206 and not determine whether the ultrasound beam should be subsequently re-steered. Or, in some embodiments, the process 200 may proceed from act 206 to act 202. In other words, after a monitoring period, the ultrasound system may perform a wide sweep rather than a narrow sweep. In some embodiments, acts 212-214 may be absent. For example, the ultrasound system may configure the ultrasound device to collect ultrasound data from a particular region scanned in act 208 regardless of whether ultrasound data collected in act 208 exceeds a threshold quality.

Figure 3:
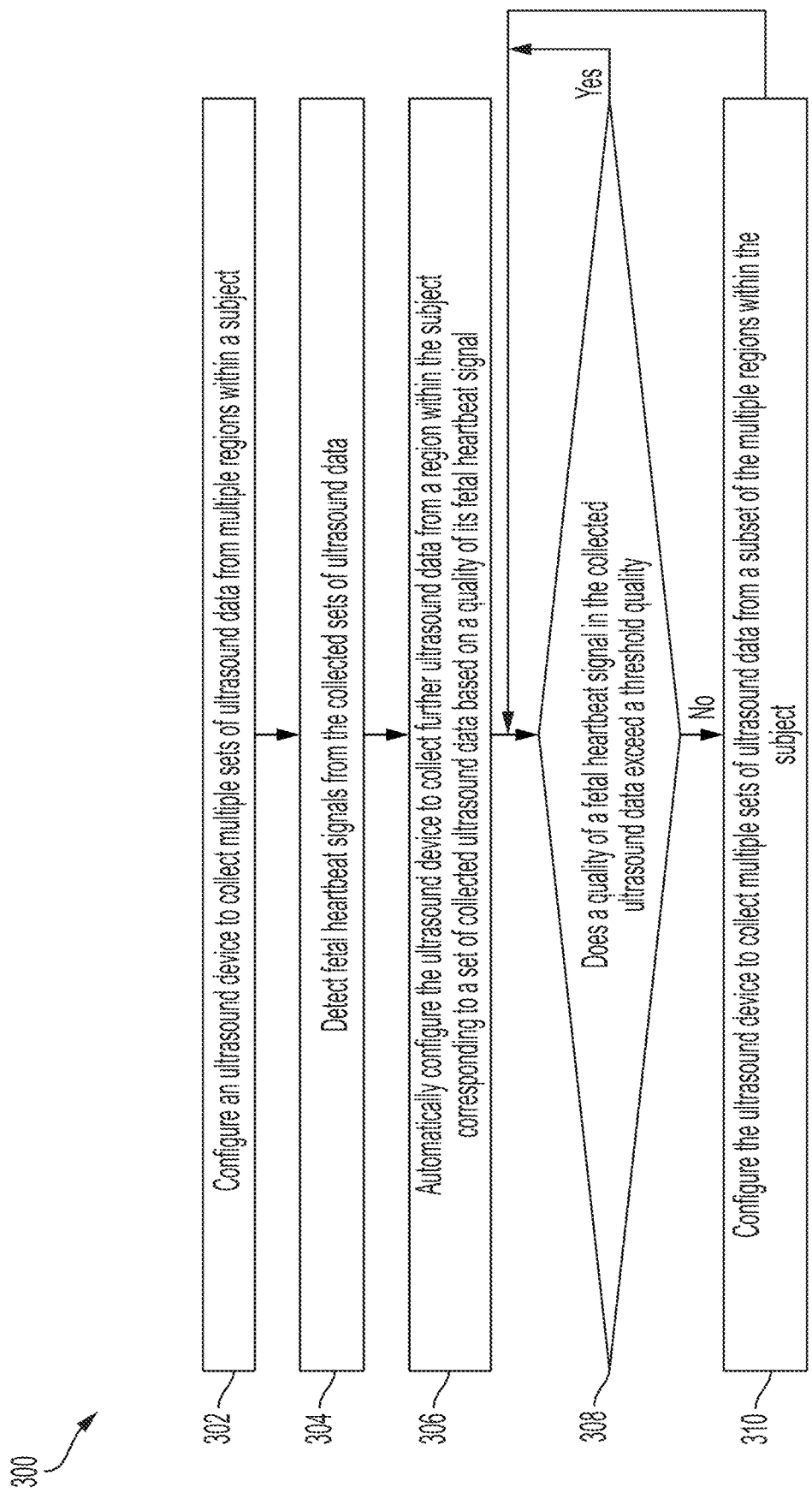
FIG. 3 is another flow diagram illustrating an example process for monitoring a fetal heartbeat or uterine contraction signal, in accordance with certain embodiments described herein.

Referring now to FIG. 3, in the process 300, act 302 may correspond to act 102, act 304 may correspond to act 104, acts 306-308 may correspond to act 106, and act 310 may correspond to act 108.

In act 302, the ultrasound system configures an ultrasound device to collect multiple sets of ultrasound data from multiple regions within a subject. Further description of act 302 may be found with reference to act 202. The process 300 proceeds from act 302 to act 304.

In act 304, the ultrasound system detects fetal heartbeat signals from the collected sets of ultrasound data. Further description of act 304 may be found with reference to act 204. The process 300 proceeds from act 304 to act 306.

In act 306, the ultrasound system automatically configures the ultrasound device to collect further ultrasound data from a region within the subject corresponding to a set of ultrasound data based on a quality of its fetal heartbeat signal. Further description of act 306 may be found with reference to act 306. The process 300 proceeds from act 306 to act 308.

In act 308, the ultrasound system determines whether a quality of a fetal heartbeat signal in the collected sets of ultrasound data (from act 306) exceeds a threshold quality. Further description of act 308 may be found with reference to act 212. In some embodiments, the ultrasound system may perform act 308 continuously on ultrasound data collected in act 306. In some embodiments, the ultrasound system may perform act 308 periodically on ultrasound data collected in act 306. If the ultrasound system determines that a quality of a fetal heartbeat signal in the collected ultrasound data exceeds a threshold quality, the process 300 repeats act 308, in which the ultrasound system continues to collect the fetal heartbeat signal and determine if the quality of the collected fetal heartbeat signal exceeds a threshold quality or not. If the ultrasound system determines that a quality of fetal heartbeat signal in the collected ultrasound data does not exceed a threshold quality, the process 300 proceeds from act 308 to act 310.

In act 310, the ultrasound system configures the ultrasound device to collect multiple sets of ultrasound data from a subset of the multiple regions within the subject. Further description of act 310 may be found with reference to act 208. Act 310 includes performing a modified sweep compared with the sweep of act 302. In some embodiments, the ultrasound system may configure the ultrasound device to collect ultrasound data from X % (where X is a number between 0 and 100) of the regions from which ultrasound data was collected in act 302. In some embodiments, the subset of the regions may be the first X % of the regions that are centered around the monitored region. If, on the next iteration through act 308, the ultrasound system determines that a quality of fetal heartbeat signal in the collected ultrasound data does not exceed a threshold quality, in act 310, the ultrasound system may configure the ultrasound device to collect ultrasound data from the next Y % (where Y is a number between 0 and 100−X) of the regions from which ultrasound data was collected in the previous iteration through act 310.

In some embodiments, acts 308-310 may be absent. For example, the ultrasound system may configure the ultrasound device to collect ultrasound data from a particular region in act 306 and not determine whether the ultrasound beam should be subsequently re-steered. Or, in some embodiments, the process 300 may proceed from act 306 to act 302. In other words, after a monitoring period, the ultrasound system may perform a wide sweep rather than a narrow sweep.

It should be appreciated that in the process 300, during monitoring of the fetal heartbeat signal, the ultrasound system may continuously or periodically monitor the quality of the signal. If the quality of signal falls below a threshold, the ultrasound system may perform a modified sweep to search for a new region from which to measure the fetal heartbeats. Otherwise, the ultrasound system may continue to monitor the signal from the same location. In contrast, in the process 200, the ultrasound system may perform the modified sweep after a monitoring period whether or not the quality of the signal has fallen below a threshold.

Figure 4:
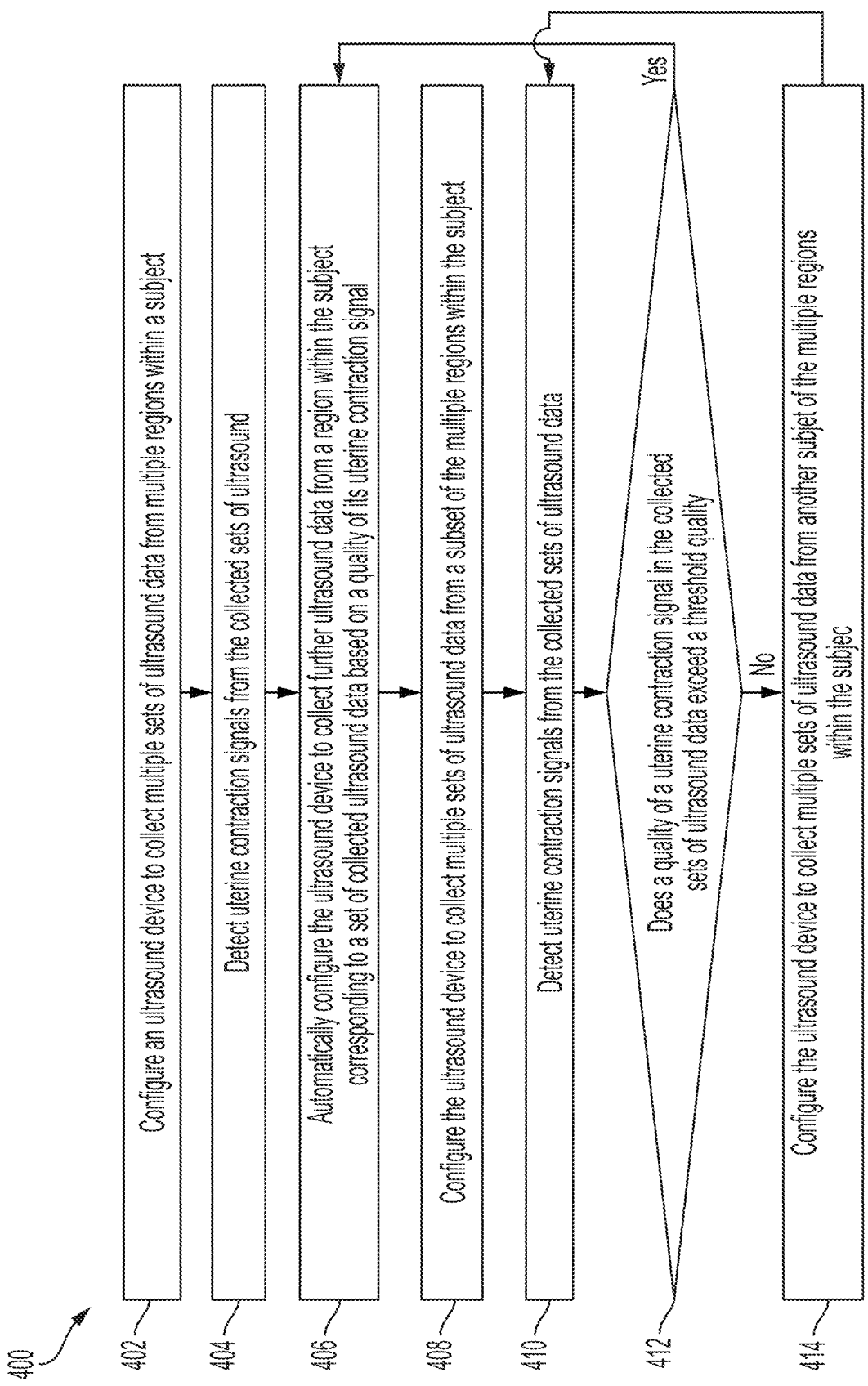
FIG. 4 is another flow diagram illustrating an example process for monitoring a fetal heartbeat or uterine contraction signal, in accordance with certain embodiments described herein.

Referring now to FIG. 4, the process 400 is the same as the process 200, except that in the process 400, the ultrasound system searches for and monitors a uterine contraction signal rather than a fetal heartbeat signal. In some embodiments, detecting uterine contraction signals (e.g., in acts 404, 406, 410) may include using a speckle tracking technique to analyze ultrasound data for tissue contraction.

In embodiments in which the ultrasound data includes A-lines, the ultrasound system may use speckle tracking techniques applied directly to the A-lines. In embodiments in which the ultrasound data includes ultrasound images from two-dimensional slices, the speckle tracking techniques may be applied to the two-dimensional ultrasound images. In some embodiments, detecting uterine contraction signals may include using a statistical model that is trained to measure the thickness of the muscle around the uterus in ultrasound images. The ultrasound system may detect contractions by detecting changes in thickness (as determined by the statistical model) that exceed a threshold. In some embodiments, the quality of a uterine contraction signal (as determined in acts 406 and 412) may be based on the signal-to-noise ratio (SNR) of the uterine contraction signal (e.g., the SNR of the speckle tracking data from which the uterine contraction signal is determined). In some embodiments, the quality of a uterine contraction signal may be based on the level of confidence of a statistical model that the statistical model has accurately measured the thickness of the muscle around the uterus. In some embodiments, detecting the uterine contraction signals and/or determining the quality of the uterine contraction signal may be performed by the ultrasound device. In some embodiments, detecting the uterine contraction signals and/or determining the quality of the uterine contraction signal may be performed by a processing device in communication with the ultrasound device.

In some embodiments, acts 408-414 may be absent. For example, the ultrasound system may configure the ultrasound device to collect ultrasound data from a particular region in act 406 and not determine whether the ultrasound beam should be subsequently re-steered. Or, in some embodiments, the process 400 may proceed from act 406 to act 402. In other words, after a monitoring period, the ultrasound system may perform a wide sweep rather than a narrow sweep. In some embodiments, acts 412-414 may be absent. For example, the ultrasound system may configure the ultrasound device to collect ultrasound data from a particular region scanned in act 408 regardless of whether ultrasound data collected in act 408 exceeds a threshold quality.

Figure 5:
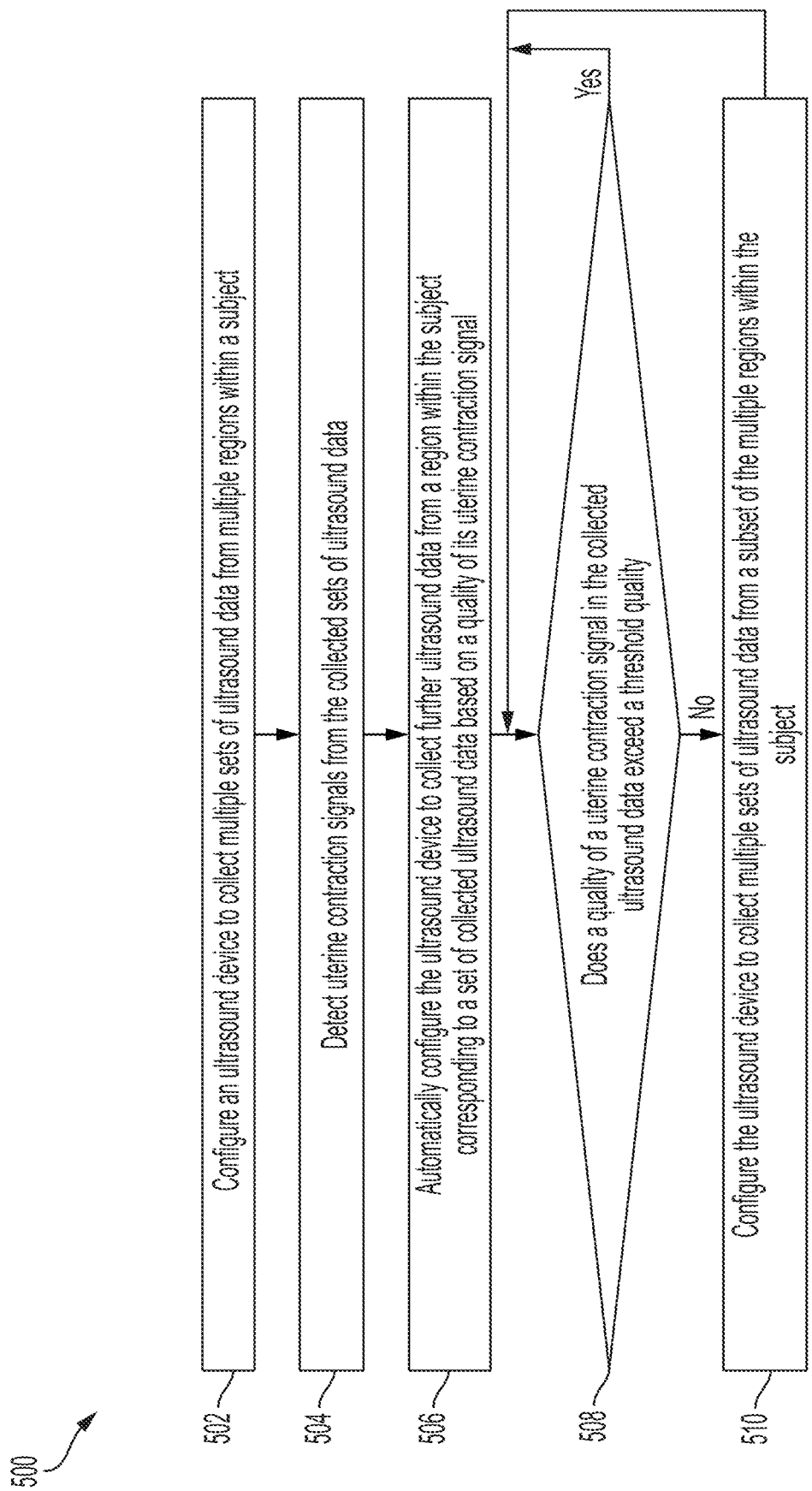
FIG. 5 is another flow diagram illustrating an example process for monitoring a fetal heartbeat or uterine contraction signal, in accordance with certain embodiments described herein.

Referring now to FIG. 5, the process 500 is the same as the process 300, except that in the process 500, the ultrasound system searches for and monitors and uterine contraction signal rather than a fetal heartbeat signal. Further description of detecting uterine contraction signals (e.g., in acts 504 and 506) and determining the quality of a uterine contraction signal (as determined in acts 506 and 508) may be found with reference to the process 400. In some embodiments, detecting the uterine contraction signals and/or determining the quality of the uterine contraction signal may be performed by the ultrasound device. In some embodiments, detecting the uterine contraction signals and/or determining the quality of the uterine contraction signal may be performed by a processing device in communication with the ultrasound device.

In some embodiments, acts 508-510 may be absent. For example, the ultrasound system may configure the ultrasound device to collect ultrasound data from a particular region in act 506 and not determine whether the ultrasound beam should be subsequently re-steered. Or, in some embodiments, the process 500 may proceed from act 506 to act 502. In other words, after a monitoring period, the ultrasound system may perform a wide sweep rather than a narrow sweep In some embodiments, either the process 200 or 300 may be combined with either the process 400 or 500. For example, the ultrasound system may perform acts 202-204 and 402-404 (i.e., searching for fetal heartbeat and uterine contraction signals with a wide sweep) and then perform acts 206 and 406 (i.e., monitoring the fetal heartbeat and uterine contraction signals). It should be appreciated that the ultrasound system may monitor the fetal heartbeat and uterine contraction signals from different regions within the subject. In other words, the ultrasound system may steer an ultrasound beam to one region to monitor the fetal heartbeat signal and steer the ultrasound beam to another region to monitor the uterine contraction signal. It should also be appreciated that the ultrasound system may monitor (i.e., in act 206) the fetal heartbeat signal at a higher sampling rate than the sampling rate at which the uterine contraction signal is monitored (i.e., in act 406) because the heartrate may be faster than the rate of contractions. For example, the sampling rate for the fetal heartbeat signal may be approximately 20-30 frames of ultrasound data per second and the sampling rate for the uterine contraction signal may be approximately 1 frame of ultrasound data per second. The ultrasound system may then perform acts 208-214 and 408-414 (i.e., searching for fetal heartbeat and uterine contraction signals with a narrow sweep) and then perform acts 206 and 406 (i.e., monitoring the fetal heartbeat and uterine contraction signals) again.

As another example, the ultrasound system may perform acts 302-304 and 502-504 (i.e., searching for fetal heartbeat and uterine contraction signals with a wide sweep) and then perform acts 306 and 506 (i.e., monitoring the fetal heartbeat and uterine contraction signals). It should be appreciated that the ultrasound system may monitor the fetal heartbeat and uterine contraction signals from different regions within the subject. In other words, the ultrasound system may steer an ultrasound beam to one region to monitor the fetal heartbeat and steer the ultrasound beam to another region to monitor the uterine contraction signal. It should also be appreciated that the ultrasound system may monitor (i.e., in act 306) the fetal heartbeat signal at a higher sampling rate than the sampling rate at which the uterine contraction signal is monitored (i.e., in act 506) because the heartrate may be faster than the rate of contractions. For example, the sampling rate for the fetal heartbeat signal may be approximately 20-30 frames of ultrasound data per second and the sampling rate for the uterine contraction signal may be approximately 1 frame of ultrasound data per second. The ultrasound system may then perform acts 308 and 508 (i.e., determine whether to search for the fetal heartbeat or uterine contraction signal with a narrow sweep) and perform acts 310 and/or 410 (i.e., perform the narrow sweep) depending on the result of acts 308 and 508. For example, the ultrasound system may re-steer the ultrasound beam just for monitoring the fetal heartbeat signal, but not re-steer the ultrasound beam for monitoring the uterine contraction signal, or vice versa.

Figure 6:
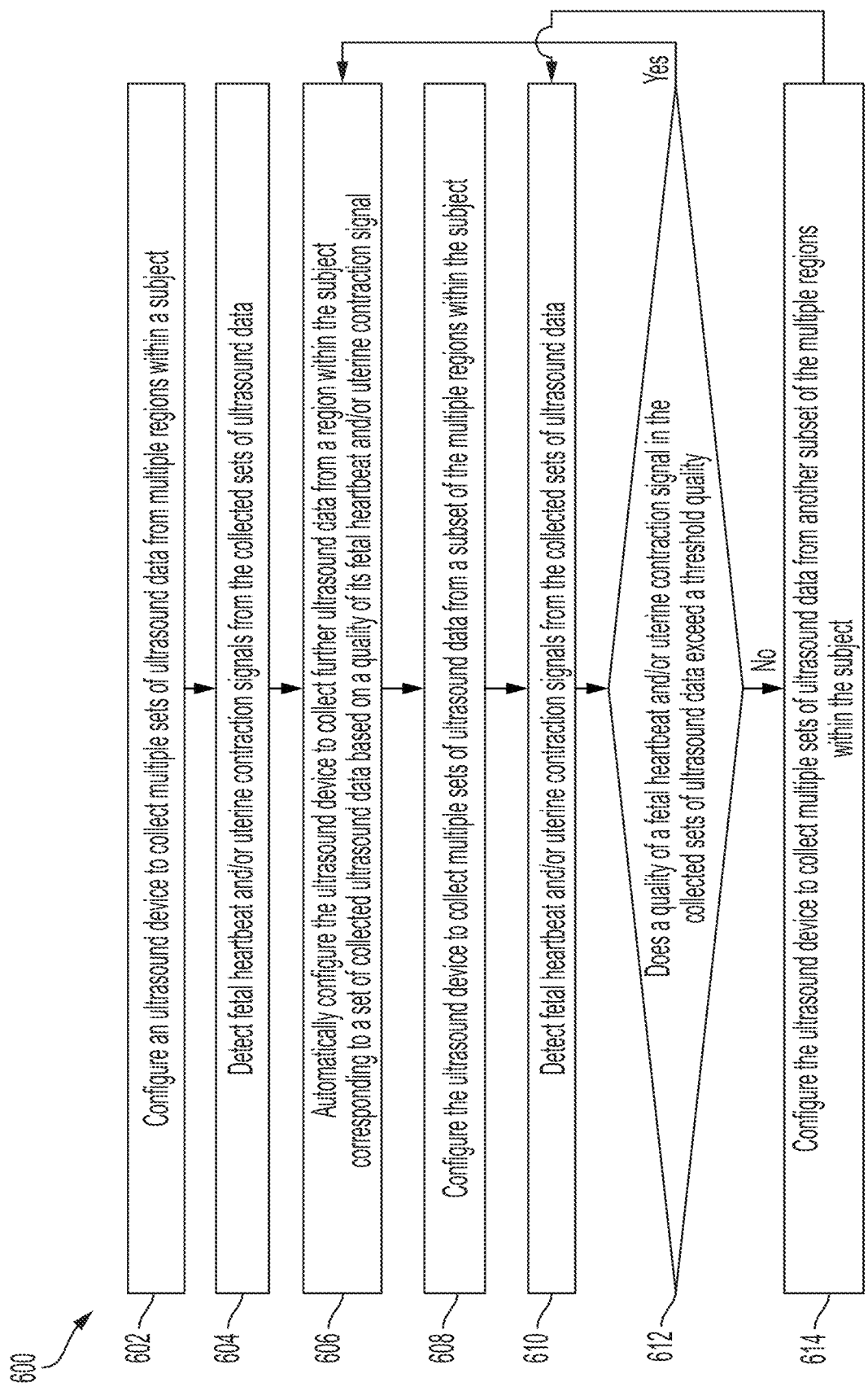
FIG. 6 is another flow diagram illustrating an example process for monitoring a fetal heartbeat or uterine contraction signal, in accordance with certain embodiments described herein.

Referring now to FIG. 6, the process 600 is the same as the processes 200 and 400, with the following differences. In acts 604 and 610, the ultrasound system detects fetal heartbeat and/or uterine contraction signals from the collected sets of ultrasound data. Further description of detecting fetal heartbeat signals may be found with reference to the process 200. Further description of detecting fetal heartbeat signals may be found with reference to the process 400. In some embodiments, the ultrasound system may detect both fetal heartbeat and uterine contraction signals from the collected sets of ultrasound data. In some embodiments, the ultrasound system may detect either fetal heartbeat or uterine contraction signals from the collected sets of ultrasound data.

In act 606, the ultrasound system automatically configures the ultrasound device to collect further ultrasound data from a region within the subject corresponding to a set of ultrasound data based on a quality of its fetal heartbeat and/or uterine contraction signal. Further description of determining the quality of a fetal heartbeat signal and configuring the ultrasound device may be found with reference to the process 200. Further description of determining the quality of a uterine contraction signal and configuring the ultrasound device may be found with reference to the process 400. In some embodiments, the region may be the region from which the set of ultrasound data having the highest quality fetal heartbeat signal was collected. In some embodiments, the region may be the region from which the set of ultrasound data having the highest quality uterine contraction signal was collected. In some embodiments, the region may be the region from which the set of ultrasound data having the highest combined quality of its fetal heartbeat and uterine contraction signals was collected. For example, the combined quality may be the mean (e.g., arithmetic or geometric) of the quality of the fetal heartbeat signal and the quality of the uterine contraction signal. It should also be appreciated that the ultrasound system may monitor fetal heartbeat signal at a higher sampling rate than the sampling rate at which the uterine contraction signal is monitored because the heartrate may be faster than the rate of contractions. For example, the sampling rate for the fetal heartbeat signal may be approximately 20-30 frames of ultrasound data per second and the sampling rate for the uterine contraction signal may be approximately 1 frame of ultrasound data per second.

In act 612, the ultrasound system determines if a quality of a fetal heartbeat and/or uterine contraction signal in the collected sets of ultrasound data exceed a threshold quality. In some embodiments, the process 600 may proceed to act 614 if the quality of the fetal heartbeat signal does not exceed a threshold quality, and otherwise proceed to act 606. In some embodiments, the process 600 may proceed to act 614 if the quality of the uterine contraction signal does not exceed a threshold quality, and otherwise proceed to act 606. In some embodiments, the process 600 may proceed to act 614 if either the quality of the fetal heartbeat signal or the quality of the uterine contraction signal does not exceed a threshold quality, and otherwise proceed to act 606. In some embodiments, the process 600 may proceed to act 614 if a combined quality of the fetal heartbeat signal and quality of the uterine contraction signal does not exceed a threshold quality, and otherwise proceed to act 606. For example, the combined quality may be the mean (e.g., arithmetic or geometric) of the quality of the fetal heartbeat signal and the quality of the uterine contraction signal. In some embodiments, determining the quality may be performed by the ultrasound device. In some embodiments, determining the quality may be performed by a processing device in communication with the ultrasound device.

In some embodiments, acts 608-614 may be absent. For example, the ultrasound system may configure the ultrasound device to collect ultrasound data from a particular region in act 606 and not determine whether the ultrasound beam should be subsequently re-steered. Or, in some embodiments, the process 600 may proceed from act 606 to act 602. In other words, after a monitoring period, the ultrasound system may perform a wide sweep rather than a narrow sweep. In some embodiments, acts 612-614 may be absent. For example, the ultrasound system may configure the ultrasound device to collect ultrasound data from a particular region scanned in act 608 regardless of whether ultrasound data collected in act 608 exceeds a threshold quality.

Figure 7:
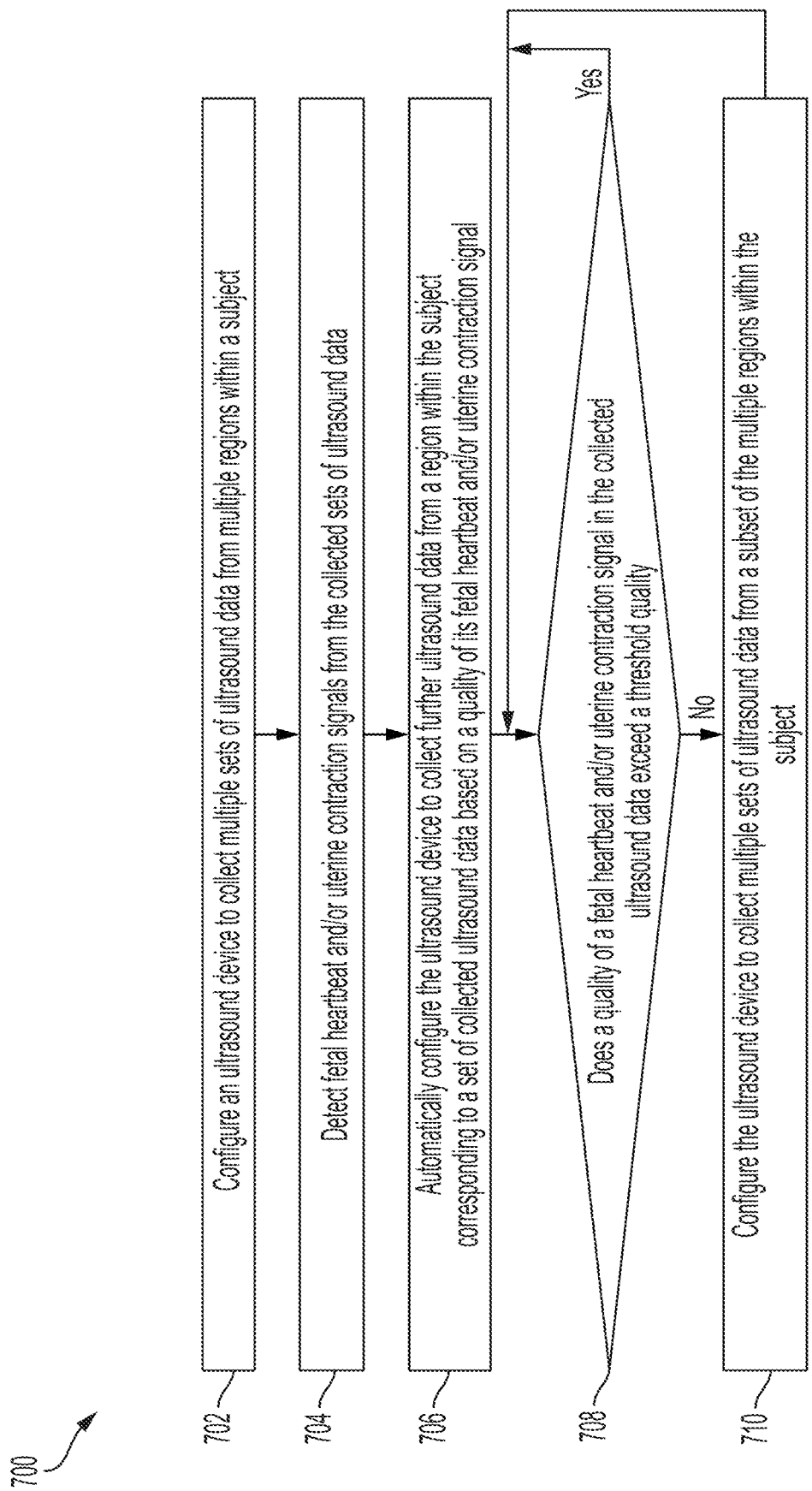
FIG. 7 is another flow diagram illustrating an example process for monitoring a fetal heartbeat or uterine contraction signal, in accordance with certain embodiments described herein.

Referring now to FIG. 7, the process 700 is the same as the processes 300 and 500, with the following differences. In act 704, the ultrasound system detects fetal heartbeat and/or uterine contraction signals from the collected sets of ultrasound. Further description of detecting fetal heartbeat signals may be found with reference to the process 200. Further description of detecting fetal heartbeat signals may be found with reference to the process 400. In some embodiments, the ultrasound system may detect both fetal heartbeat and uterine contraction signals from the collected sets of ultrasound data. In some embodiments, the ultrasound system may detect either fetal heartbeat or uterine contraction signals from the collected sets of ultrasound data.

In act 706, the ultrasound system automatically configures the ultrasound device to collect further ultrasound data from a region within the subject corresponding to a set of ultrasound data based on a quality of its fetal heartbeat and/or uterine contraction signal. Further description of determining the quality of a fetal heartbeat signal may be found with reference to the process 200. Further description of determining the quality of a uterine contraction signal may be found with reference to the process 400. In some embodiments, the region may be the region from which the set of ultrasound data having the highest quality fetal heartbeat signal was collected. In some embodiments, the region may be the region from which the set of ultrasound data having the highest quality uterine contraction signal was collected. In some embodiments, the region may be the region from which the set of ultrasound data having the highest combined quality of its fetal heartbeat and uterine contraction signals was collected. For example, the combined quality may be the mean (e.g., arithmetic or geometric) of the quality of the fetal heartbeat signal and the quality of the uterine contraction signal. It should be appreciated that the ultrasound system may monitor the fetal heartbeat and uterine contraction signals from the same region within the subject. It should also be appreciated that the ultrasound system may monitor the fetal heartbeat signal at a higher sampling rate, such as 20-30 frames of ultrasound data per second, than the sampling rate at which the uterine contraction signal is monitored, such as 1 frame of ultrasound data per second, because the heartrate may be faster than the rate of contractions.

In act 708, the ultrasound system determines if a quality of a fetal heartbeat and/or uterine contraction signal in the collected sets of ultrasound data exceed a threshold quality. In some embodiments, the process 700 may proceed to act 710 if the quality of the fetal heartbeat signal does not exceed a threshold quality, and otherwise continue with act 708. In some embodiments, the process 700 may proceed to act 710 if the quality of the uterine contraction signal does not exceed a threshold quality, and otherwise continue with act 708. In some embodiments, the process 700 may proceed to act 710 if either the quality of the fetal heartbeat signal or the quality of the uterine contraction signal does not exceed a threshold quality, and otherwise continue with act 708. In some embodiments, the process 700 may proceed to act 710 if a combined quality of the fetal heartbeat signal and quality of the uterine contraction signal does not exceed a threshold quality, and otherwise continue with act 708. For example, the combined quality may be the mean (e.g., arithmetic or geometric) of the quality of the fetal heartbeat signal and the quality of the uterine contraction signal. In some embodiments, determining the quality may be performed by the ultrasound device. In some embodiments, determining the quality may be performed by a processing device in communication with the ultrasound device.

In some embodiments, acts 708-710 may be absent. For example, the ultrasound system may configure the ultrasound device to collect ultrasound data from a particular region in act 506 and not determine whether the ultrasound beam should be subsequently re-steered. Or, in some embodiments, the process 700 may proceed from act 706 to act 702. In other words, after a monitoring period, the ultrasound system may perform a wide sweep rather than a narrow sweep.

It should be appreciated that monitoring the fetal heartbeat and uterine contraction signals may happen at the same time within the same device. In some embodiments, as described above with reference to the processes 200-500, monitoring the fetal heartbeat and uterine contraction signals may be done by switching back and forth between monitoring the fetal heartbeat signal and monitoring the uterine contraction signal. For example, the system may find the heartbeat signal, then find the contraction signal, then find the heartbeat signal, etc. In some embodiments, uterine contraction monitoring may occur less frequently, as described above. In some embodiments, monitoring the fetal heartbeat and uterine contraction signals may be done by interleaving. For example, some of the transmit events (e.g., performed in the configuration and detection acts in the processes 600 and 700) may be performed for monitoring the fetal heartbeat signal, and some transmit events may be performed for monitoring the uterine contraction signal. Transmit events for monitoring a specific signal may not necessarily be grouped together in time, as the processing routines may separate the data corresponding to the fetal heartbeat and uterine contraction signals upon collection. In some embodiments, monitoring the fetal heartbeat and the uterine contraction signals may include using the same ultrasound data. For example, certain transmit events or every transmit event (e.g., performed in the configuration and detection acts in the processes 600 and 700) may be used by the processing to detect either or both the fetal heartbeat signal and the uterine contraction signal.

In some embodiments, during monitoring of a fetal heartbeat and/or uterine contraction signal (e.g., in acts 106, 206, 306, 406, 506, 606, and 706), the ultrasound device may output the fetal heartbeat and/or uterine contraction signal for display. For example, the ultrasound device may transmit the fetal heartbeat and/or uterine contraction signals over a communication link to a processing device, which may then display the fetal heartbeat signal or the uterine contraction signal as one or more graphs on its display screen. As described above, the processing device may be, for example, a mobile phone, tablet, laptop, the processing device of a standard cardiotocography system, or another type of electronic device. In some embodiments, the ultrasound patch device may transmit the fetal heartbeat and/or uterine contraction signal over a wired communication link (e.g., over Ethernet, a Universal Serial Bus (USB) cable or a Lightning cable). In some embodiments, the ultrasound patch device may transmit the fetal heartbeat and/or uterine contraction signal over a wireless communication link (e.g., over a BLUETOOTH, WiFi, ZIGBEE, or cellular (e.g., 3G, LTE, or CAT-M1) wireless communication link). In embodiments in which the processing device is a processing device of a standard CTG system, the ultrasound device may include an output port configured to couple to one end of a cable, the other end of which is configured be coupled to the processing device of the CTG system. For example, in the case of USB communication, the ultrasound device may include a USB port and circuitry capable of communication according to the USB protocol. The processing device of the cardiotocography system may then display the fetal heartbeat and/or uterine contraction signal. In other words, the ultrasound device described herein, rather than the cardiotocography system's own transducer, may transmit the fetal heartbeat and/or uterine contraction signal to the processing device of the cardiotocography system for display. In some embodiments, the processing device may process and/or condition the fetal heartbeat and/or uterine contraction signals prior to display.

In some embodiments, instead of or in addition to the processes 100-700, the ultrasound system may configure the ultrasound device to collect a time series of ultrasound data, where the ultrasound data at each point in time at which it is collected is from a three-dimensional volume in the subject. The ultrasound system may detect the fetal heartbeat and/or uterine contraction signals from the three-dimensional volume, using the methods described above (e.g., with reference to the processes 200 and 400). The ultrasound data from the three-dimensional volume at each point in time at which it is collected may be collected using a wide sweep (e.g., as described in act 102). Assuming that the three-dimensional volume encompasses the appropriate regions within the subject where the fetal heartbeat and/or uterine contraction signal can be detected, it may not be necessary to steer an ultrasound beam to a particular region to monitor the fetal heartbeat and/or uterine contraction signal (e.g., as described in act 106) nor may it be necessary to perform a narrow sweep to re-steer the ultrasound beam (e.g., as described in act 108). In some embodiments, undersampling or three-dimensional plane wave reconstruction with a low number of transmit plane angles may be used to collect the time series of three-dimensional data at a sufficiently high rate to detect the fetal heartbeat.

As described above, any of the statistical models described in this application may be stored and run on the ultrasound device. For example, the ultrasound device may include one or more chips designed for operating statistical models. The chips may be artificial intelligence (AI) accelerator chips, such as tensor processing units (TPUs)). Any of the analyses described herein, such as detecting fetal heartbeat signals and/or uterine contraction signals, determining fetal heart rate, detecting medically noteworthy signals, and/or determining the quality of fetal heartbeat and/or uterine contraction signals, may be performed on the ultrasound device (and may or may not include use of statistical models). The ultrasound device may be considered self-contained in that it may perform all the described analysis on the device, rather than transmitting data to an external processing device for analysis.

Figure 8:
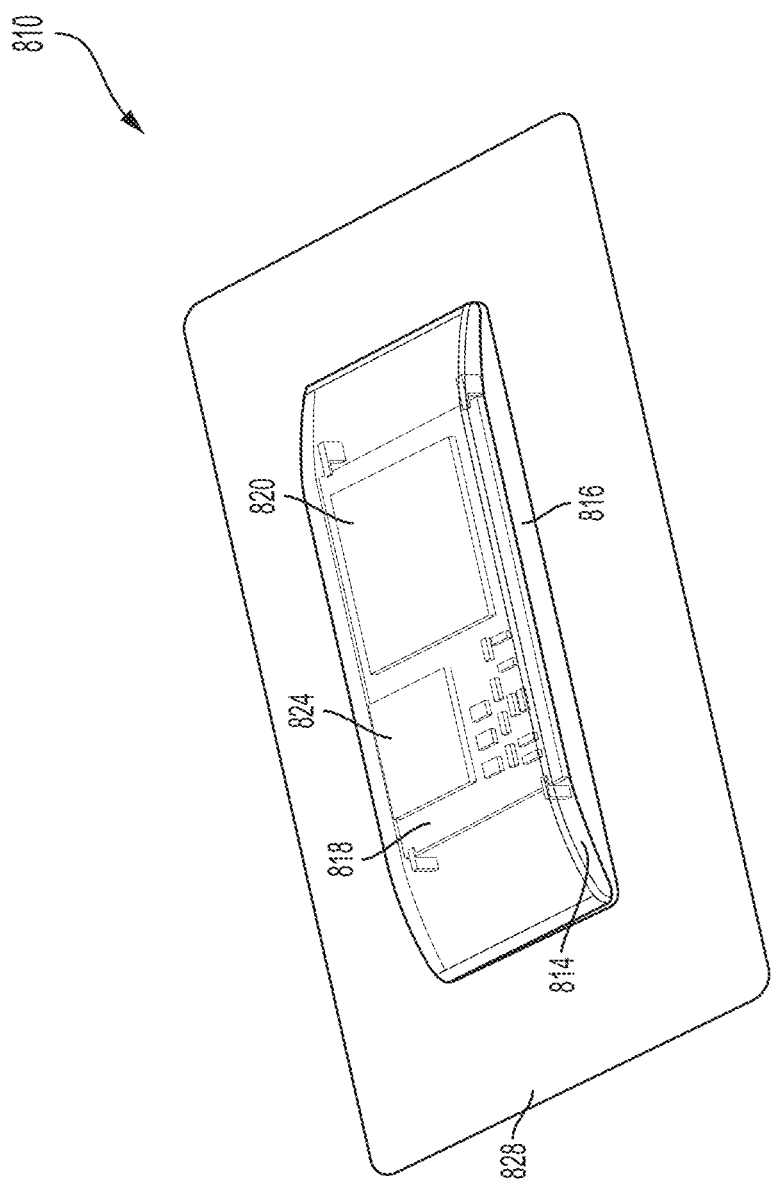
FIG. 8 is a perspective view an example ultrasound patch, in accordance with certain embodiments described herein.

FIG. 8 is a perspective view of an example ultrasound patch 810, in accordance with certain embodiments described herein. The ultrasound patch 810 includes an upper housing 814, a lower housing 816, a circuit board 818, and a dressing 828. For purposes of illustration, the upper housing 814 of the ultrasound patch 810 is depicted in a transparent manner to depict exemplary locations of various internal components of the ultrasound patch 810. The circuit board 818 supports a heat sink 820 and communications circuitry 824.

In some embodiments, the communication circuitry 824 includes one or more short- or long-range communication platforms. Exemplary short-range communication platforms include Bluetooth (BT), Bluetooth Low Energy (BLE), and Near-Field Communication (NFC). Exemplary long-range communication platforms include WiFi and Cellular (e.g., 3G, LTE, or CAT-M1). While not shown, the communication circuitry 824 may include front-end radio, antenna and other processing circuitry configured to communicate radio signals to an external processing electronic device (not shown). In some embodiments, the ultrasound patch 810 may be configured, using the communication circuitry 824, to wirelessly offload signals (e.g., fetal heartbeat and/or uterine contraction signals) collected by the ultrasound patch 810 to a processing device (not shown) for further processing, display, and/or storage. In some embodiments, the ultrasound patch 810 may offload the signals to the processing device in real-time. The ultrasound patch 810 may receive, with the communication circuitry 824, control parameters communicated from the processing device to the ultrasound patch 810. The control parameters may dictate the scope of the ultrasound data/image to be obtained by ultrasound patch 810. The circuit board 818 may further include processing circuitry (not shown), including one or more controllers and/or field-programmable gate arrays (FPGAs) to direct communication through the communication circuitry 824. The dressing 828 may provide an adhesive surface for adhering the ultrasound patch 810 (in particular, the lower housing 816) to the skin of a patient. One non-limiting example of such a dressing 828 is Tegaderm™, a transparent medical dressing available from 3M Corporation.

Figure 9:
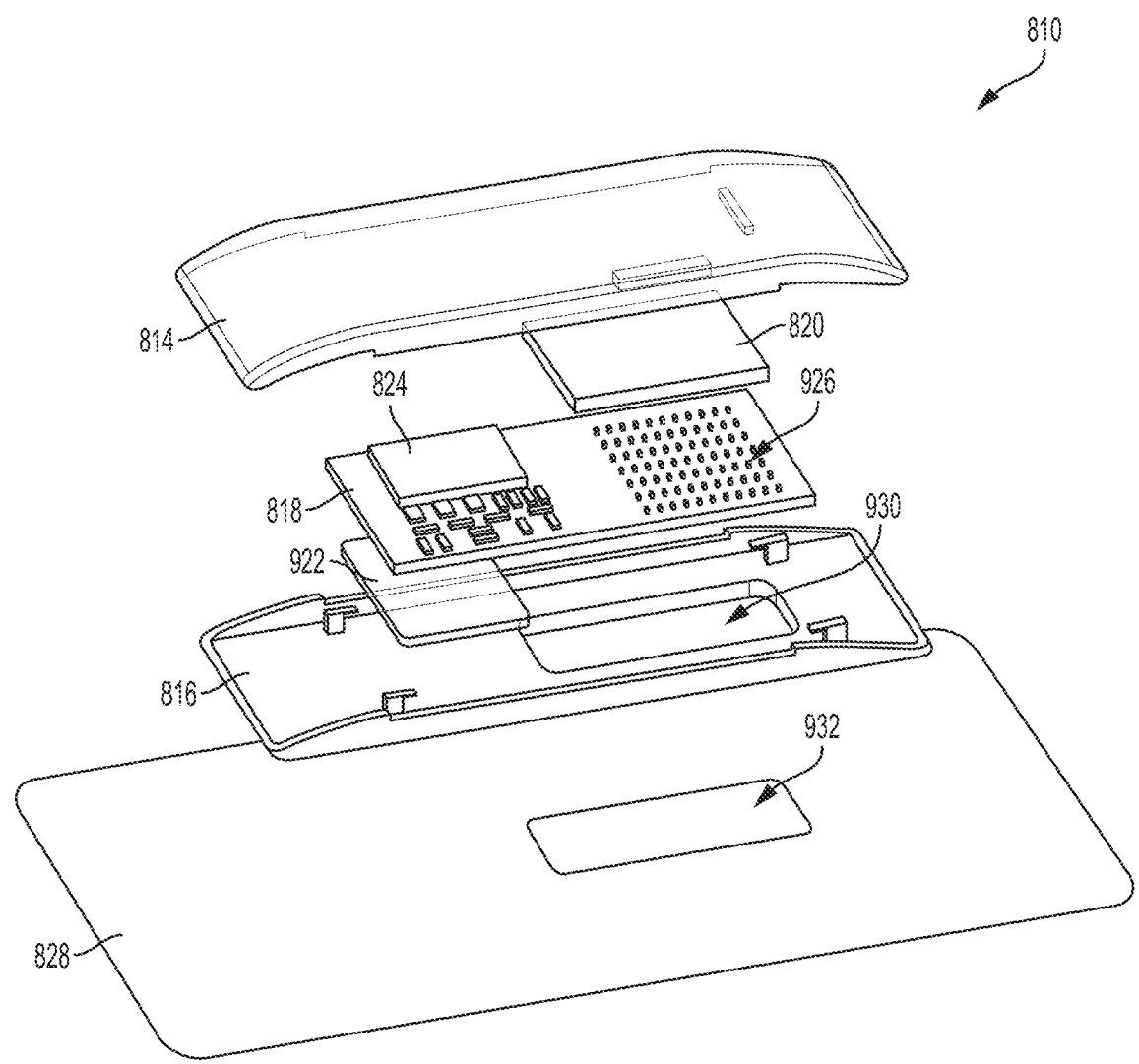
FIG. 9 is an exploded view of the ultrasound patch of FIG. 8, in accordance with certain embodiments described herein.

FIG. 9 is an exploded view of the ultrasound patch 810 in accordance with certain embodiments described herein. FIG. 9 illustrates a plurality of through vias 926 (e.g., copper) that may be used for a thermal connection between the heat sink 820 and one or more CMOS chips (not shown in FIG. 9, but shown as 1034 in FIG. 10). The lower housing 816 includes an opening 930 that aligns with another opening 932 in the dressing 828. FIG. 9 further illustrates that the circuit board 818 supports a battery 922.

Figure 10:
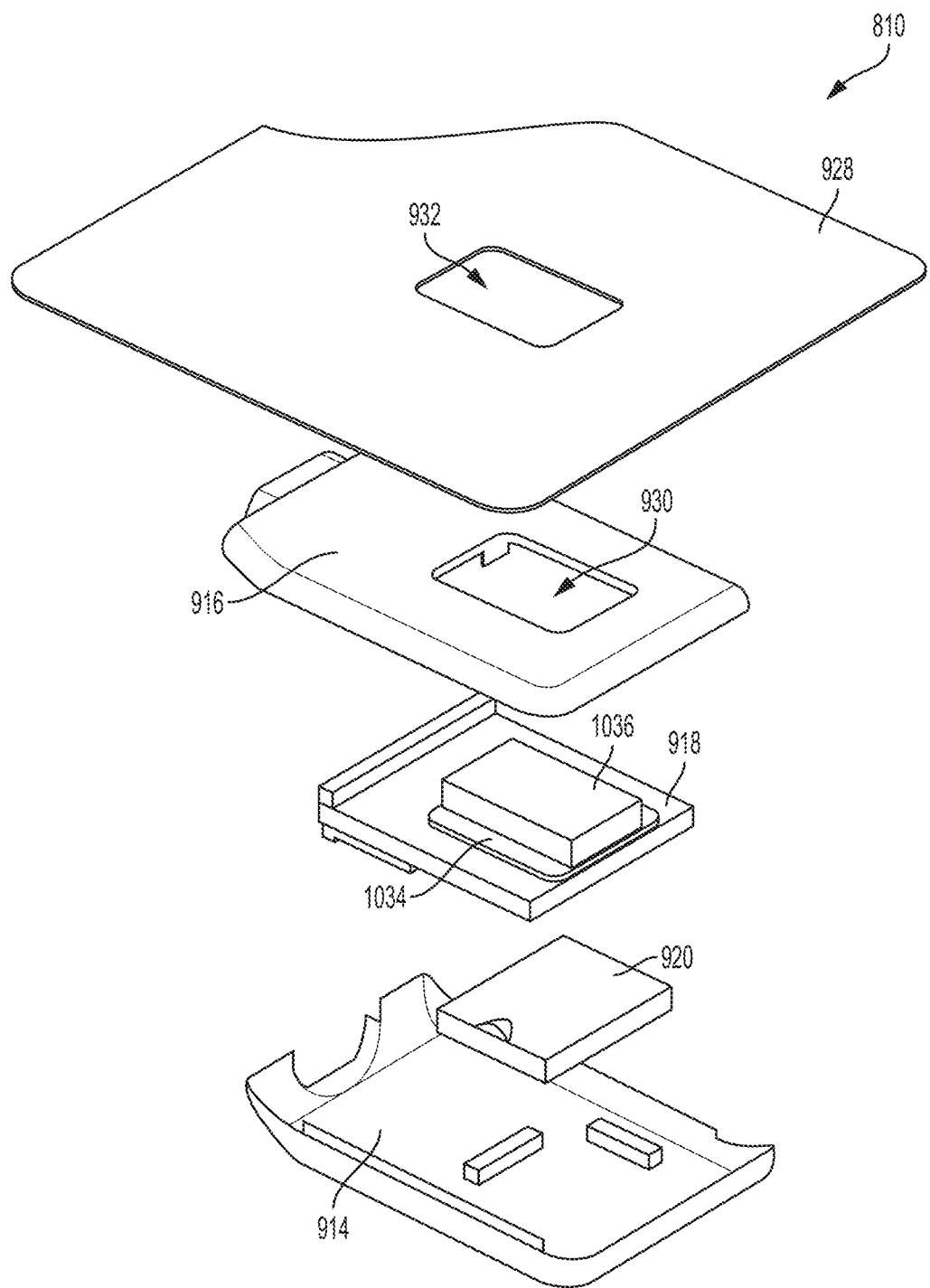
FIG. 10 is another exploded view of the ultrasound patch of FIG. 8, in accordance with certain embodiments described herein.

FIG. 10 is another exploded view of the ultrasound patch 810, in accordance with certain embodiments described herein. FIG. 10 illustrates the location of an integrated CMOS chip 1034 on the circuit board 818. For example, the CMOS chip 1034 may be a chip including ultrasound transducers and an application-specific integrated circuit (ASIC). The CMOS chip 1034 may be an ultrasound-on-chip (i.e., a device including micromachined ultrasound transducers integrated with an ASIC or other semiconductor die containing integrated circuitry). In some embodiments, the CMOS chip 1034 may instead be multiple chips packaged together (e.g., in a stacked configuration). Further description of the CMOS chip 1034 in certain embodiments may be found in U.S. patent application Ser. No. 15/626,711 titled "UNIVERSAL ULTRASOUND DEVICE AND RELATED APPARATUS AND METHODS," filed on Jun. 19, 2017 and published as U.S. Pat. App. Publication No. 2017-0360399 A1 and/or U.S. patent application Ser. No. 16/192,603 titled "ULTRASOUND APPARATUSES AND METHODS FOR FABRICATING ULTRASOUND DEVICES," filed on Nov. 15, 2018 and published as U.S. Pat. App. Publication No. 2019-0142387 A1. FIG. 10 further illustrates an acoustic lens 1036 mounted over the CMOS chip 1034. The acoustic lens 1036 may be configured to protrude through openings 930 and 932 to make contact with the skin of a patient.

Figure 11:
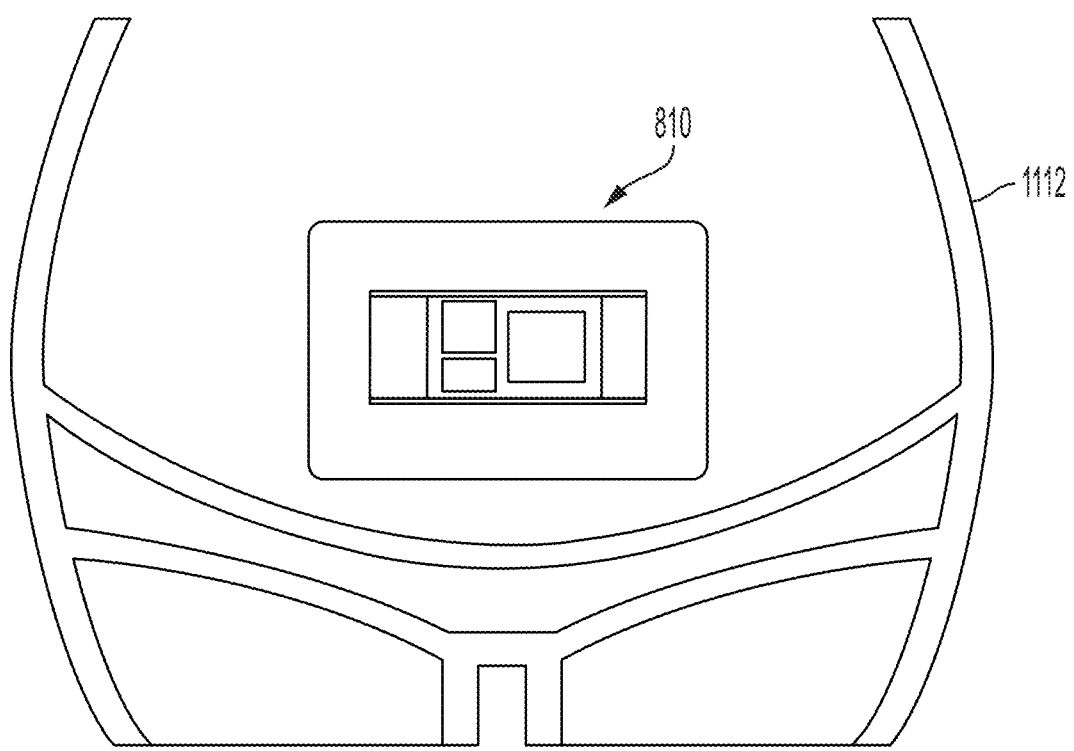
FIG. 11 is an illustration of the ultrasound patch of FIG. 8 coupled to a patient, in accordance with certain embodiments described herein.

FIG. 11 is an illustration of the ultrasound patch 810 coupled to a patient 1112, in accordance with certain embodiments described herein. FIG. 11 illustrates the ultrasound patch 810 coupled to a region adjacent to the uterus of the patient 1112, such that the ultrasound patch 810 may detect fetal heartbeat and/or uterine contraction signals.

Figure 12:
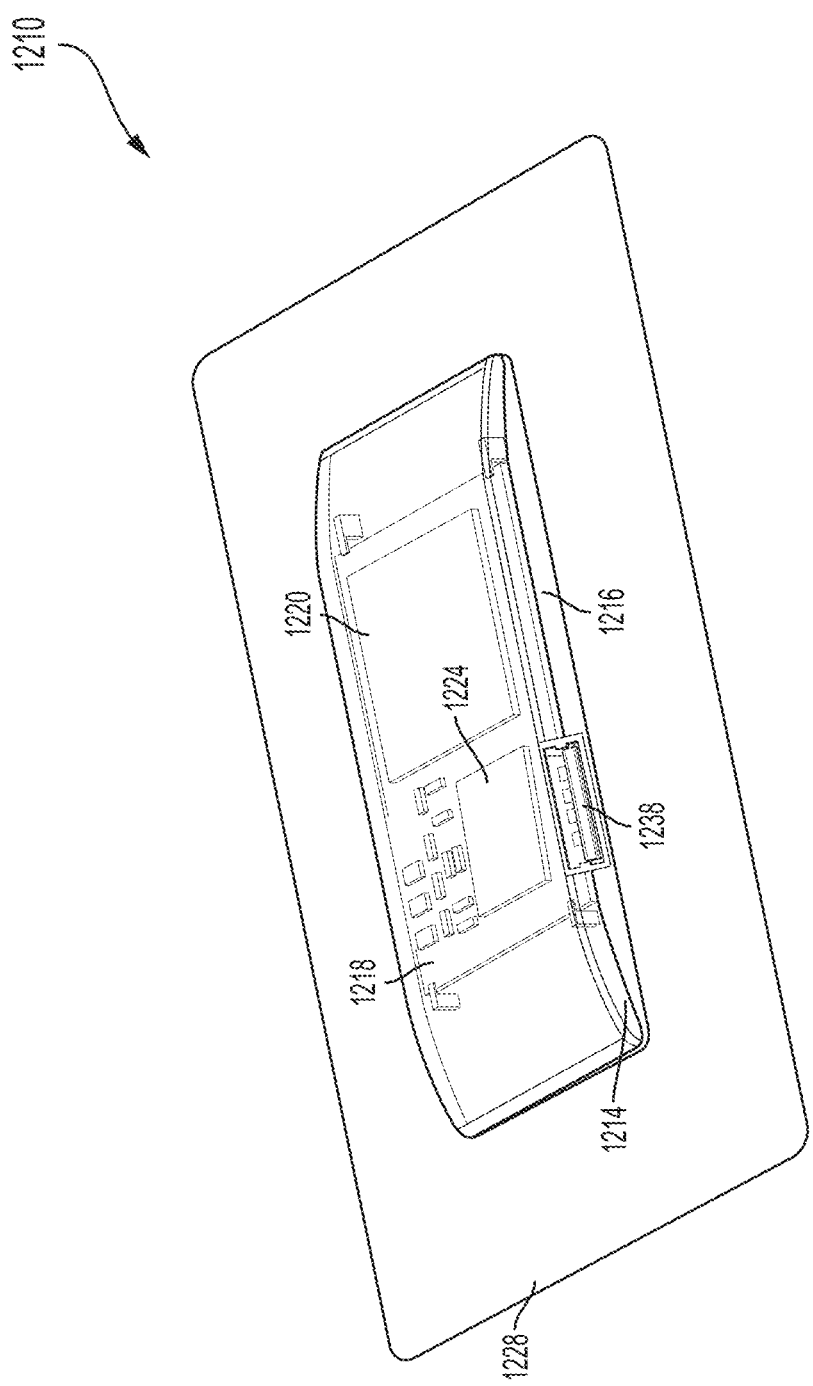
FIG. 12 is a perspective view of another example ultrasound patch, in accordance with certain embodiments described herein.

FIG. 12 is a perspective view of an example ultrasound patch 1210, in accordance with certain embodiments described herein. The ultrasound patch 1210 includes an upper housing 1214, a lower housing 1216, a circuit board 1218, a dressing 1228, a heat sink 1220, and communications circuitry 1224. The upper housing 1214 and the lower housing 1216 differ from the upper housing 814 and the lower housing 816 in that the upper housing 1214 and the lower housing 1216 include a port 1238 disposed in an opening in the upper housing 1214 and lower housing 1216 (or, in some embodiments, just one of the housings). The port 1238 may be configured to accept one end of a cable. For example, in the case of USB communication, the port 1238 may be a USB port configured to accept one end of a USB cable. The other end of the cable may be configured to couple to a processing device. The processing device may be, for example, a mobile phone, tablet, laptop, the processing device of a standard cardiotocography system, or another type of electronic device. The communications circuitry 1224 may be configured to transmit and receive data through the port 1238. For example, the communications circuitry 1224 may be configured to transmit and receive data according to a certain protocol, such as the Universal Serial Bus (USB) protocol. The circuit board 1218 supports the communications circuitry 1224 and the heat sink 1220. Further description of the dressing 1228 may be found with reference to the dressing 828. Additionally, the circuit board 1218 may support a CMOS chip (e.g., the CMOS chip 1034) which is not be visible in FIG. 12.

Figure 13:
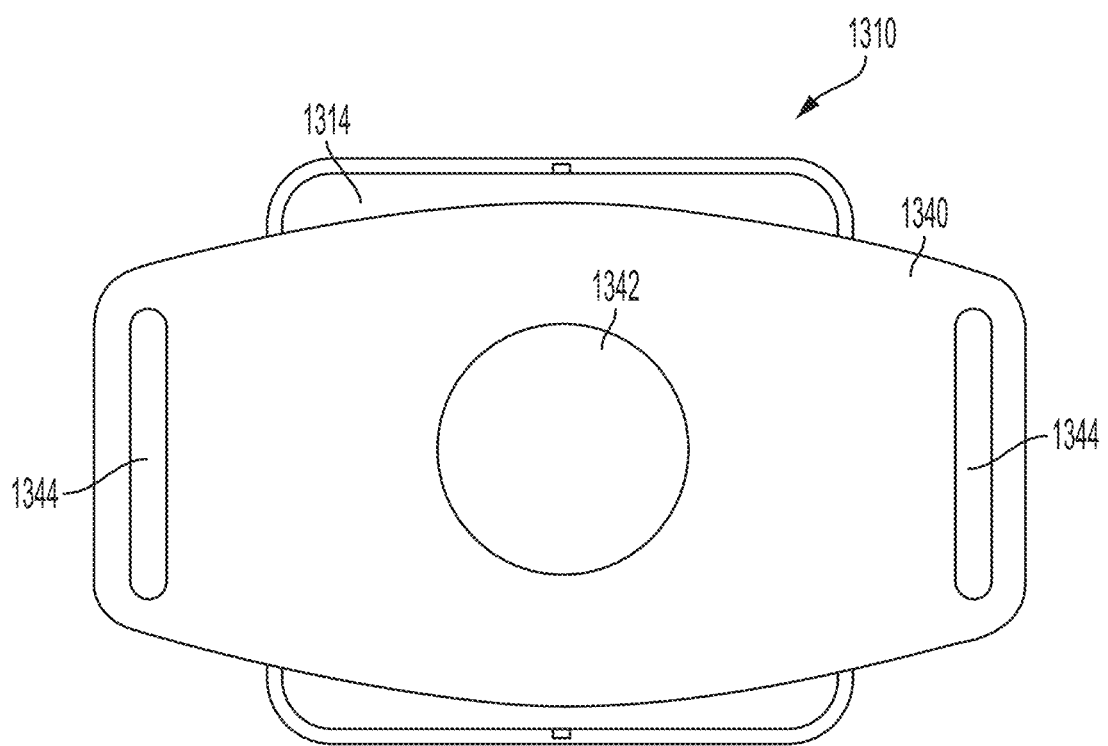
FIG. 13 is an illustration of an example alternative fastening mechanism for an ultrasound patch, in accordance with certain embodiments described herein.

FIG. 13 illustrates an example alternative fastening mechanism for an ultrasound patch 1310 in accordance with certain embodiments described herein. The ultrasound patch 1310 may be the ultrasound patch 810 or the ultrasound patch 1210, for example. The ultrasound patch 1310 includes a top housing 1314, which may be the top housing 814 or the top housing 1214. The fastening mechanism includes a buckle 1340, a post 1342, and slots 1344. The top housing 1314 is affixed to the buckle 1340 via the post 1342 using, for example, a threaded engagement between the buckle 1340 and the post 1342. Other attachment configurations are also contemplated, however. The buckle 1342 includes slots 1344 for accommodating a strap.

Figure 14:
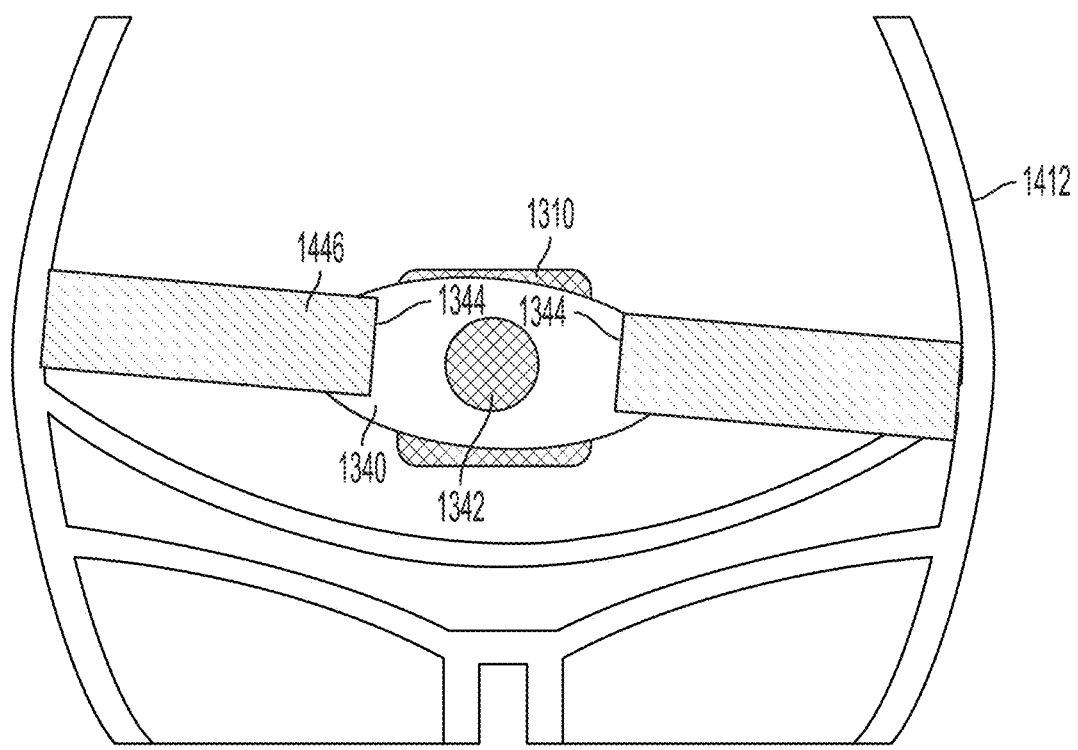
FIG. 14 is an illustration of the ultrasound patch of FIG. 13 fastened to a patient, in accordance with certain embodiments described herein.

FIG. 14 is an illustration of the ultrasound patch 1310 fastened to a patient 1412, in accordance with certain embodiments described herein. FIG. 14 illustrates a strap 1446 threaded through the slots 1344, wrapped around the patient 1412, and appropriately tightened in order to secure the ultrasound patch 1310 to the desired region of the patient 1412. In FIG. 14, the ultrasound patch 1310 is secured to a region adjacent to the uterus of the patient 1412, such that the ultrasound patch 1310 may detect fetal heartbeat and/or uterine contraction signals.

Figure 15:
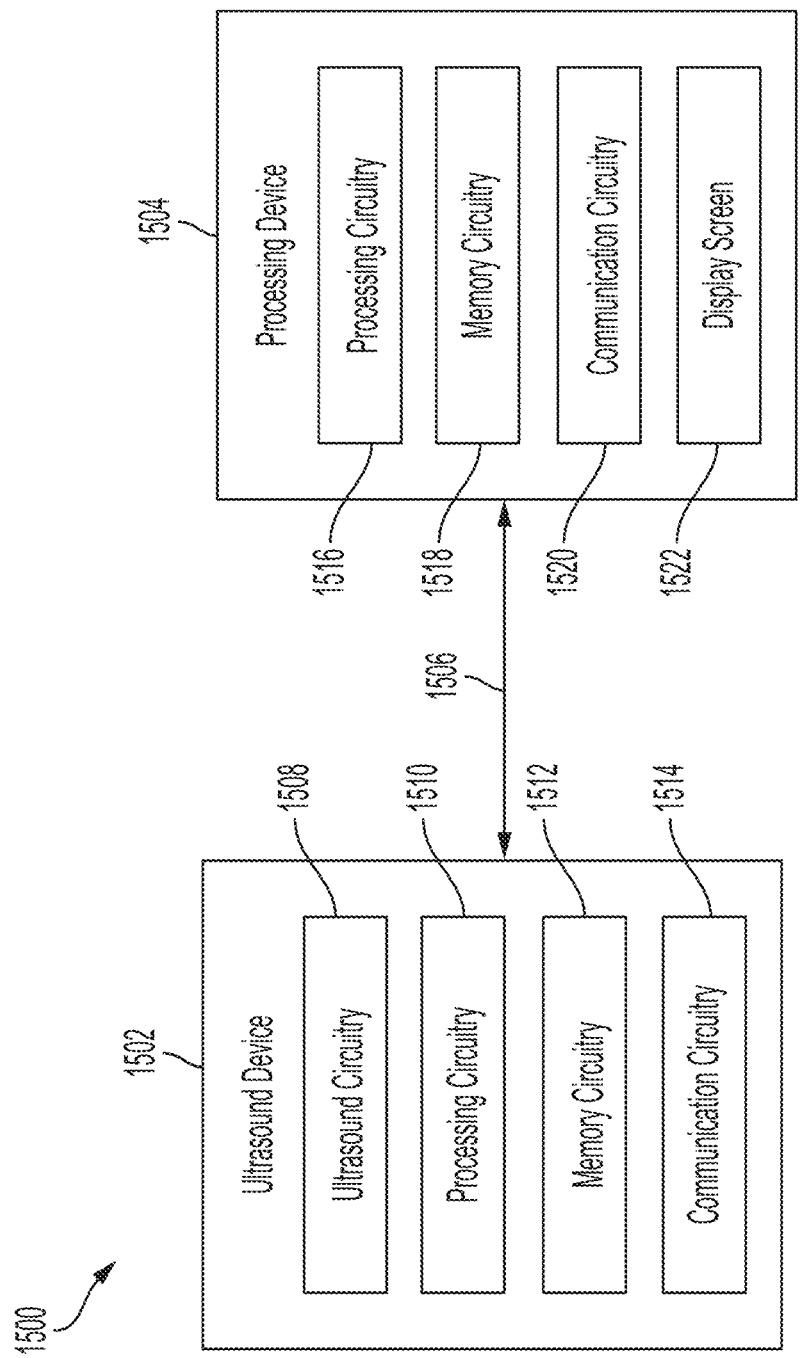
FIG. 15 is a schematic block diagram of an example ultrasound system, in accordance with certain embodiments described herein.

FIG. 15 is a schematic block diagram of an example ultrasound system 1500, in accordance with certain embodiments described herein. As shown, the ultrasound system 1500 includes an ultrasound device 1502, a processing device 1504, and a communication link 1506. The ultrasound device 1502 may be any of the ultrasound devices (e.g., a wearable ultrasound device, such as a patch) described herein. The processing device 1504 may be any of the processing devices described herein. The ultrasound device 1502 includes ultrasound circuitry 1508, processing circuitry 1510, memory circuitry 1512, and communication circuitry 1514. The processing device 1504 includes processing circuitry 1516, memory circuitry 1518, communication circuitry 1520, and a display screen 1522. The ultrasound device 1502 is configured to communicate with the processing device 1504 over the communication link 1506. The communication link 1506 may include a wired connection and/or a wireless connection. The ultrasound device 1502 may be any of the ultrasound devices described herein. The processing device 1504 may be any of the processing devices described herein.

The ultrasound device 1502 may be configured to generate ultrasound data that may be employed to generate an ultrasound image. The ultrasound device 1502 may be constructed in any of a variety of ways. In some embodiments, the ultrasound device 1502 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 1508 may be configured to generate the ultrasound data. The ultrasound circuitry 1508 may include an ultrasound-on-chip, and thus may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 1508 (e.g., transmit circuitry, receive circuitry, control circuitry, power management circuitry, and processing circuitry) to form a monolithic ultrasound device. In some embodiments, the ultrasound transducers may be arranged in an array, such as a two-dimensional array. The two-dimensional array of ultrasound transducers may enable the ultrasound circuitry 1508 to steer ultrasound beams in different directions (e.g., to steer the ultrasound beams at different azimuthal and elevational angles) and thereby collect three-dimensional ultrasound data of a volume within a subject.

The processing circuitry 1510 may control operation of the ultrasound device 1502, and in particular, operation of the ultrasound circuitry 1508, the memory circuitry 1512, and the communication circuitry 1514. As one example, the processing circuitry 1510 may be configured to control collection of ultrasound data by the ultrasound device 1502. As another example, the processing circuitry 1510 may be configured to store and operate any of the statistical models described herein. The portion of the processing circuitry 1510 configured to store and operate statistical models may be implemented as artificial intelligence (AI) accelerator chips, which may include one or more tensor processing units (TPUs). TPUs may be application-specific integrated circuits (ASICs) specifically designed for operating statistical models, machine learning, and/or deep learning. The TPUs may be employed to, for example, accelerate the inference phase of a neural network. The memory circuitry 1512 may include non-transitory computer-readable storage media. The processing circuitry 1510 may control writing data to and reading data from the memory circuitry 1512 in any suitable manner. To perform any of the functionality of the ultrasound device 1502 described herein, the processing circuitry 1510 may execute one or more processor-executable instructions stored in one or more non-transitory computer-readable storage media (e.g., the memory circuitry 1512), which may serve as non-transitory computer-readable storage media storing processor-executable instructions for execution by the processing circuitry 1510. The communication circuitry 1514 may be configured to enable communication between the ultrasound device 1502 and the processing device 1504 over the communication link 1506. The communication circuitry 1514 may include an antenna and circuitry capable of transmitting and receiving signals according to a certain wireless communication protocol (e.g., WiFi, BLUETOOTH, Zigbee, or cellular (e.g., 3G, LTE, or CAT-M1) and/or a data connector port for accepting a data connector of a particular type and circuitry capable of transmitting and receiving signals according to a certain protocol. In some embodiments, the communication circuitry 1514 may include circuitry for communication according to multiple protocols and/or circuitry for wired and wireless communication. The ultrasound device 1502 may be configured as a wearable ultrasound device, such as a patch. Wearable ultrasound devices are described further with reference to FIGS. 8-14.

The processing device 1504 may be configured to process ultrasound data from the ultrasound device 1502 to generate ultrasound images. The processing may be performed by, for example, the processing circuitry 1516. The processing circuitry 1516 may also be adapted to control the acquisition of ultrasound data with the ultrasound device 1502. The ultrasound data may be processed in real-time during a scanning session as the echo signals are received. In some embodiments, the displayed ultrasound image may be updated at a rate of at least 5 Hz, at least 10 Hz, at least 20 Hz, at a rate between 5 and 60 Hz, at a rate of more than 20 Hz, etc. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing circuitry 1516 of the processing device 1504 may also be configured to control operation of the processing device 1504. The processing circuitry 1516 may be configured to control operation of the memory circuitry 1518, the communication circuitry 1520, and the display screen 1522. The memory circuitry 1518 may include non-transitory computer-readable storage media. The processing circuitry 1516 may control writing data to and reading data from the memory circuitry 1518 in any suitable manner. To perform any of the functionality of the processing device 1504 described herein, the processing circuitry 1516 may execute one or more processor-executable instructions stored in one or more non-transitory computer-readable storage media (e.g., the memory circuitry 1518), which may serve as non-transitory computer-readable storage media storing processor-executable instructions for execution by the processing circuitry 1516.

The communication circuitry 1520 may be configured to enable communication between the processing device 1504 and the ultrasound device 1502 over the communication link 1506. When the communication circuitry 1520 is configured for wired communication, the communication circuitry 1520 may include a data connector port for accepting a data connector of a particular type and circuitry capable of transmitting and receiving signals according to a certain protocol. For example, in the case of USB communication, the communication circuitry 1520 may include a USB port and circuitry capable of communication according to the USB protocol. When the communication circuitry 1520 is configured for wireless communication, the communication circuitry 1520 may include an antenna and circuitry capable of transmitting and receiving signals according to a certain protocol. In some embodiments, the communication circuitry 1520 may include circuitry for communication according to multiple protocols and/or circuitry for wired and wireless communication. The display screen 1522 may be configured to display images and/or videos, and may be, for example, a liquid crystal display (LCD), a plasma display, and/or an organic light emitting diode (OLED) display on the processing device 1504.

It should be appreciated that the processing device 1504 may be implemented in any of a variety of ways. For example, the processing device 1504 may be implemented as a handheld device such as a mobile smartphone or a tablet, as a portable device that is not a handheld device such as a laptop, or as a stationary device such as a desktop computer or the processing device of a standard cardiotocography system.

For further description of ultrasound devices and systems, as well as description of ultrasound-on-chips, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application) and/or U.S. patent application Ser. No. 16/192,603 titled "ULTRASOUND APPARATUSES AND METHODS FOR FABRICATING ULTRASOUND DEVICES," filed on Nov. 15, 2018 and published as U.S. Pat. App. Publication No. 2019-0142387 A1, which are incorporated by reference herein in their entireties.

FIG. 15 should be understood to be non-limiting. For example, the ultrasound system 1500, the ultrasound device 1502, and the processing device 1504 may include fewer or more components than shown.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
an ultrasound system configured to:
configure a wearable ultrasound patch coupled to a subject to collect multiple sets of ultrasound data from multiple regions within the subject;
detect fetal heartbeat and uterine contraction signals from the collected sets of ultrasound data;
subsequent to detection of a fetal heartbeat signal, monitor the fetal heartbeat signal by automatically configuring the wearable ultrasound patch to steer an ultrasound beam to a first region within the subject to collect further ultrasound data from the first region corresponding to one of the multiple sets of ultrasound data based on a quality of the fetal heartbeat signal; and subsequent to detection of a uterine contraction signal, monitor the uterine contraction signal by automatically configuring the wearable ultrasound patch to steer the ultrasound beam to a second region within the subject to collect further ultrasound data from the second region within the subject corresponding to one of the multiple sets of ultrasound data based on a quality of the uterine contraction signal.

2. The apparatus of claim 1, wherein the ultrasound system is configured to monitor the fetal heartbeat signal and the uterine contraction signal at the same time.

3. The apparatus of claim 1, wherein the ultrasound system is configured to monitor the fetal heartbeat signal and the uterine contraction signal alternately.

4. The apparatus of claim 1, wherein the wearable ultrasound patch comprises a two-dimensional array of ultrasonic transducers.

5. The apparatus of claim 1, wherein each of the multiple sets of ultrasound data comprises a time series of an A-line.

6. The apparatus of claim 1, wherein each of the multiple sets of ultrasound data comprises a time series of ultrasound images collected from a two-dimensional slice within the subject.

7. The apparatus of claim 1, wherein the ultrasound system is configured, when detecting the fetal heartbeat signals from the collected sets of ultrasound data, to use an M-mode ultrasound technique.

8. The apparatus of claim 1, wherein the ultrasound system is configured, when automatically configuring the wearable ultrasound patch to steer the ultrasound beam to the first region to collect the further ultrasound data from the first region corresponding to one of the multiple sets of ultrasound data based on the quality of the fetal heartbeat signal, to configure the wearable ultrasound patch to use a two-dimensional array of ultrasonic transducers to steer the ultrasound beam in three dimensions to the first region in order to collect the further ultrasound data.

9. The apparatus of claim 1, wherein the ultrasound system is configured, when automatically configuring the wearable ultrasound patch to steer the ultrasound beam to the first region to collect the further ultrasound data from the first region corresponding to one of the multiple sets of ultrasound data based on the quality of the fetal heartbeat signal, to configure the wearable ultrasound patch to collect the further ultrasound data without collecting ultrasound data from other of the multiple regions within the subject.

10. The apparatus of claim 1, wherein:
the ultrasound system is configured, when automatically configuring the wearable ultrasound patch to steer the ultrasound beam to the first region to collect the further ultrasound data from the first region corresponding to one of the multiple sets of ultrasound data based on the quality of the fetal heartbeat signal, to configure the wearable ultrasound patch to collect the further ultrasound data from a region within the subject corresponding to a set of ultrasound data that has a highest quality fetal heartbeat signal or a highest combined quality of fetal heartbeat and uterine contraction signals; and
the ultrasound system is configured, when automatically configuring the wearable ultrasound patch to steer the ultrasound beam to the second region to collect the further ultrasound data from the second region corresponding to one of the multiple sets of ultrasound data based on a quality of the uterine contraction signal, to configure the wearable ultrasound patch to collect the further ultrasound data from a region within the subject corresponding to a set of ultrasound data that has a highest quality uterine contraction signal or a highest combined quality of fetal heartbeat and uterine contraction signals.

11. The apparatus of claim 1, wherein the ultrasound system is further configured to:
continuously or periodically monitor a quality of the fetal heartbeat and/or uterine contraction signals; and
configure the ultrasound device to collect multiple sets of ultrasound data from a subset of the multiple regions within the subject based on the quality of the fetal heartbeat and/or uterine contraction signals not exceeding a threshold quality.

12. The apparatus of claim 11, wherein the subset of the regions is a first particular percentage of regions approximately centered around the first and/or second region within the subject from which the further ultrasound data was collected.

13. The apparatus of claim 11, wherein the subset of the regions is along a spiral curve around the first and/or second region within the subject from which the further ultrasound data was collected.

14. The apparatus of claim 1, wherein the ultrasound system is configured to determine whether to re-steer the ultrasound beam to a different region than the first and/or second region based on the quality of the fetal heartbeat signal and/or the uterine contraction signal.

15. The apparatus of claim 1, wherein the ultrasound system is configured to monitor the fetal heartbeat signal at a higher sampling rate than a sampling rate at which the uterine contraction signal is monitored.

16. The apparatus of claim 1, wherein the ultrasound system is further configured to transmit the fetal heartbeat and uterine contraction signals over a communication link to a processing device configured to display the fetal heartbeat and uterine contraction signals as one or more graphs on its display screen.

17. The apparatus of claim 16, wherein the processing device comprises a mobile phone, tablet, laptop, or a processing device of a standard cardiotocography system.

18. An apparatus, comprising:
an ultrasound system configured to:
sweep a volume to collect ultrasound data from the subject;
detect a fetal heartbeat signal and a uterine contraction signal in the ultrasound data;
subsequent to detection of the fetal heartbeat signal, automatically configure a wearable ultrasound patch to steer an ultrasound beam to a first region within the subject to monitor the fetal heartbeat signal based on a quality of the fetal heartbeat signal; and
subsequent to detection of the uterine contraction signal, automatically configure the wearable ultrasound patch to steer the ultrasound beam to a second region within the subject to monitor the uterine contraction signal based on the quality of uterine contraction signal.

19. The apparatus of claim 18, where the ultrasound data comprises multiple sets of ultrasound data collected at different locations within the volume.

20. The apparatus of claim 18, wherein the ultrasound system is further configured to determine a location where the fetal heartbeat and/or uterine contraction signal is detectable or detectable at a highest quality.

21. The apparatus of claim 18, wherein the ultrasound system is further configured to sweep a modified volume to collect ultrasound data.

22. The apparatus of claim 21, wherein:
the ultrasound system is further configured to determine a location where the fetal heartbeat and/or uterine contraction signal is detectable or detectable at the highest quality; and
the ultrasound system is configured, when sweeping the modified volume to collect ultrasound data, to sweep a volume modified based on the location where the fetal heartbeat and/or uterine contraction signal was previously monitored.

23. The apparatus of claim 21, wherein the modified volume is collected with a sweep that is centered around the location where the fetal heartbeat uterine contraction signal was previously monitored.

* * * * *